United States Patent
Yonekawa

(12) 
(10) Patent No.: US 6,504,897 B1
(45) Date of Patent: Jan. 7, 2003

(54) X-RAY IMAGE RADIOGRAPHING SYSTEM

(75) Inventor: Hisashi Yonekawa, Hino (JP)

(73) Assignee: Konica Corporation, Tokyo (JP)

( * ) Notice: Subject to any disclaimer, the term of this patent is extended or adjusted under 35 U.S.C. 154(b) by 0 days.

(21) Appl. No.: 09/714,636

(22) Filed: Nov. 17, 2000

(30) Foreign Application Priority Data

Nov. 26, 1999 (JP) .......................................... 11-375992

(51) Int. Cl.[7] .............................................. G01N 23/02
(52) U.S. Cl. ........................... 378/63; 378/98.8; 378/57
(58) Field of Search .............................. 378/62, 63, 57, 378/98.2, 98.6, 98.8, 4, 197, 196

(56) References Cited

U.S. PATENT DOCUMENTS

| | | | | |
|---|---|---|---|---|
| 4,064,440 A | * | 12/1977 | Roder | ........................... 378/57 |
| 5,237,598 A | * | 8/1993 | Albert | ........................... 378/62 |
| 5,525,905 A | * | 6/1996 | Mohapatra et al. | ............. 378/4 |
| 5,907,593 A | * | 5/1999 | Hsieh et al. | .................... 378/4 |

* cited by examiner

*Primary Examiner*—Drew A. Dunn
(74) *Attorney, Agent, or Firm*—Finnegan, Henderson, Farabow, Garrett & Dunner, L.L.P.

(57) ABSTRACT

A X-ray image radiographing system, comprises a plurality of X-ray image output apparatus each of which detects X-rays having passed through an object and outputs image data of the object; a control apparatus to control the plurality of the X-ray image output apparatus; an object information input device to input object information regarding the radiographed object; and a storage device to store the image data outputted from the plurality of X-ray image output apparatus and the object information inputted from the object information input device, wherein the image data of the object is stored so as to be correlated with the object information of the object.

51 Claims, 10 Drawing Sheets

X-RAY IMAGE RADIOGRAPHING SYSTEM

BACKGROUND OF THE INVENTION

The present invention relates to an X-ray image radiographing system.

Recently, a tendency to digitize the X-ray image information of patients generated in the hospitals, and by storing and transmitting it, to enhance the efficiency and the speed of diagnosis, is increasing. Accordingly, also in a field of the direct radiographing, the X-ray image radiographing apparatus to output the digital data comes to be used often instead of the conventional screen/film system.

The X-ray image radiographing apparatus to output the digital data can be classified to the X-ray image radiographing apparatus using the solid-state plane detector and the X-ray image radiographing apparatus using the stimulative fluorescent substance (stimulable phosphor plate), according to the kind of the detecting means of X-ray.

In the X-ray image radiographing apparatus using the solid-state plane detector, the solid-state plane detector in which the solid-state image pick-up element, commonly called flat panel detector (FPD), is two-dimensionally arranged, is representative. In the FPD, there is a direct type FPD in which, by using a photoconductive material such as a-Se in which the electron and the electric charge of positive hole are generated by the X-ray energy, as a detecting means, the X-ray energy is directly converted into the electric charge, and the electric charge is read out as an electric signal by the reading-out element (reading-out means) such as a TFT two-dimensionally arranged in a fine area unit.

Further, an indirect type FPD in which the X-ray energy is converted into the light by a scintillator, or the like, and the converted light is converted into the electric charge by the photoelectric conversion element such as a-Si two-dimensionally arranged in a fine area unit, and the electric charge is read out as the electric signal by the reading-out element (reading-out means) such as a TFT two-dimensionally arranged in a fine area unit, which is the same as the photoelectric conversion element, is also widely known.

Further, in the present invention, an image division type FPD in which the X-ray energy is converted into the light by the scintillator, or the like, and the converted light is received by a large number of CCD or CMOS sensors which are arranged grid-like on the same plane, through a converging body such as a lens or optical fiber, and in the inside of the CCD or CMOS sensor, via photoelectric conversion, and electron·voltage conversion, it is read out as an electric signal, is also defined as one of solid state plane detectors.

On the one hand, the X-ray image radiographing apparatus using the stimulative fluorescent substance is normally called the computed radiography (CR). In the apparatus, a part of the X-ray energy transmitted through the subject is detected by a sheet-like detecting means called the stimulative fluorescent substance, and simultaneously, the detected energy is accumulated once inside the stimulative fluorescent substance. When the energy accumulated inside the stimulative fluorescent substance is excited by a predetermined wavelength of laser light, it can be taken out as the stimulation light. This stimulation light can be taken out as an electric signal by using the photoelectric conversion element such as a photo-multiplier, or the like.

Generally, the digital X-ray image radiographing apparatus forms an X-ray image radiographing system in which an X-ray image output apparatus 1, control apparatus 2, X-ray generation control apparatus 3, and X-ray tube 4 are main components, as shown in FIG. 1, FIG. 2, and FIG. 3.

Such the X-ray image radiographing system is largely classified into the exclusive-use type. X-ray image radiographing system shown in FIGS. 1 and 2 and the cassette correspondent type X-ray image radiographing system shown in FIG. 3.

In the exclusive-use type X-ray image radiographing system, because a detecting means for detecting the X-ray (detector section) is fixed or housed in the inside of the radiographing apparatus, the operator can not simply carry the detecting means. As the detecting means, any one of a solid state plane detector and stimulative fluorescent substance can be used.

On the one hand, in the cassette correspondent type X-ray image radiographing system, the X-ray detecting means is housed in a portable thin box-like case called cassette, and the operator can easily carry the X-ray detecting means together with the cassette. As the detecting means, any one of a solid state plane detector and stimulative fluorescent substance can be used.

FIG. 3 is a view showing the cassette correspondent type X-ray image radiographing system, in which the stimulative fluorescent substance is used for the X-ray detecting means. The cassette correspondent type X-ray image radiographing system using the stimulative fluorescent substance is characterized by a portable cassette 6 in which a detecting means 100 for detecting the X-ray 5, that is, the stimulative fluorescent substance plate is housed, and the X-ray image output apparatus 1 to read the X-ray image information accumulated in the stimulative fluorescent substance. In the present invention, a kind of the X-ray image output apparatus 1 used in the cassette correspondent type X-ray image radiographing system is defined as the cassette correspondent type X-ray image output apparatus.

The exclusive-use type X-ray image radiographing system is further classified into a stand alone type X-ray image radiographing system as shown in FIG. 1, and a lying type X-ray image radiographing system as shown in FIG. 2.

The stand alone type X-ray image radiographing system is characterized by an elevator stand 60 and an X-ray image output apparatus 1, as shown in FIG. 1, and is a system in which the subject 50 is radiographed in an erecting condition. Because the X-ray image output apparatus 1 is structured such that it can be moved up and down, the position of the X-ray image output apparatus 1 can be adjusted in the vertical direction corresponding to a height of the subject 50. In the present invention, as a kind of the X-ray image output apparatus 1 used in the stand alone type X-ray image radiographing system, the stand alone type X-ray image output apparatus is defined.

On the one hand, the lying type X-ray image radiographing system is characterized by a plate-like member 70, bed 80, and X-ray image output apparatus 1, and is a system in which the subject 50 is radiographed in a lying condition on the plate-like member 70. In the present invention, a kind of the X-ray image output apparatus 1 used in the lying type X-ray image radiographing system is defined as the lying type X-ray image output apparatus.

As described above, a very large number of types of X-ray image radiographing systems mixedly exist. In the hospital, a demand for a high degree diagnosis and a demand for a diagnosis responsible to various conditions of a patient are increased. Therefore, since it is difficult to cope with these demand with a single type of an apparatus, there is a trend to employ plural type of diagnostic apparatus. Further, it may happens frequently that a diagnosis for a single person is conducted by using plural types of diagnostic apparatus in order to conduct the diagnosis from various aspects. However, because different type of radiographing systems using respective detecting means are used in the individually operating condition, the present condition is in the circumstances in which the operational efficiency is bad for the operator and the operator can hardly operate the system.

However, only by combining plural systems, it may be difficult to obtain an efficient reliable system. Further, there are many problems in the operability of respective systems, and it is hard to say that the system which is easily used and reliable, can be provided to the operators (a medical X-ray technician). Especially, a disadvantage that a finish of the image radiographed between systems using the different detecting means is different from each other, also occurs. If an image is captured on these conditions and the image is provided from the operator to a doctor, there may be a fear that the reliability of the diagnosis by the doctor is lowered.

SUMMARY OF THE INVENTION

In view of such the actual situations, the present invention is attained, and an object of the present invention is to provide an X-ray image radiographing system in which the operational efficiency is good for the operator and the circumstance for easy operation can be obtained.

Further, an object of the present invention is to provide an X-ray image radiographing system which is easily used and reliable.

Further, an object of the present invention is to provide an X-ray image radiographing system by which an image of a predetermined finish can be obtained, even when the different detecting means is used.

Further, an object of the present invention is to provide an X-ray image radiographing. system in which an installation area of the apparatus is decreased, and together with it, the introduction cost is low, and which has an extendability.

In order to solve the foregoing problems and to attain the objects, the present invention is structured as follows.

(1) An X-ray image radiographing system which comprises: a plurality of X-ray image output apparatus by which, after the X-ray irradiated from the X-ray tube is detected by the detecting means, it is outputted as the digitized image data; a control apparatus to control the plurality of the X-ray image output apparatus; a patient information input means for inputting the patient information; and a storage means for storing the image data outputted from the X-ray image output apparatus and the patient information inputted from the patient information input means, wherein the patient information inputted from the patient information input means is made to correspond also to the image data outputted from any one of X-ray image output apparatus in the plurality of X-ray image output apparatus, and is stored in the storage means.

According to the invention described in (1), because the same patient information is made to correspond to the image data outputted from a plurality of X-ray image output apparatus, and can be stored, even when the same patient is radiographed by different X-ray image output apparatus, or even when the image data of the same patient is read out by the different X-ray image output apparatus, the patient information input is completed by only one time input, and a time to input the same patient information for each of X-ray image output apparatus to be used for the radiography, can be saved.

Further, because the X-ray image output apparatus can be controlled by one control apparatus, the system can be easily structured and expanded at the lower cost. Further, because one control apparatus is sufficient for a plurality of X-ray image output apparatus, the installaiton area of the control apparatus can be suppressed to the minimum.

(2) An X-ray image radiographing system which comprises: a plurality of X-ray image output apparatus by which, after the X-ray irradiated from the X-ray tube is detected by the detecting means, it is outputted as the digitized image data; a plurality of control apparatus to respectively control the plurality of the X-ray image output apparatus; a patient information input means connected to at least one of the plurality of control apparatus for inputting the patient information; and a storage means for storing the image data outputted from the plurality of X-ray image output apparatus and the patient information inputted from the patient information input means, wherein the patient information inputted from the patient information input means is made to correspond also to the image data outputted from any one of X-ray image output apparatus in the plurality of X-ray image output apparatus, and is stored in the storage means.

According to the invention described in (2), even when the plurality of X-ray image output apparatus are controlled by the plurality of control apparatus, because the patient information is held in common among plurality of control apparatus, and the same patient information is made to correspond to the image data outputted from the different X-ray image output apparatus and can be stored, even when the same patient is radiographed by different X-ray image output apparatus, or even when the image data of the same patient is read out by the different X-ray image output apparatus, the patient information input is completed by only one time input, and a time to input the same patient information for each of X-ray image output apparatus to be used for the radiography, can be saved.

(3) An X-ray image radiographing system which comprises: a plurality of X-ray image output apparatus by which, after the X-ray irradiated from the X-ray tube is detected by the detecting means, it is outputted as the digitized image data; a control apparatus to control the plurality of the X-ray image output apparatus; and the X-ray image radiographing system structured by a communication cable to connect the plurality of X-ray image output apparatus to the control apparatus, wherein the plurality of X-ray image output apparatus are successively connected onto the communication cable, and each of the plurality of X-ray image output apparatus is individually controlled by the control apparatus through the communication cable.

According to the invention described in (3), because the system is structured such that the plurality of X-ray image output apparatus are successively connected onto the communication cable, a total cable length of the communication cable can be short, and the system cost can be reduced. Further, an interface substrate on the control apparatus side can be structured by one substrate, thereby, the system cost can be further reduced. Further, because the interface of only one system may be controlled, a control program of the control apparatus is simplified, thereby, the development cost and the development load can be reduced. Further, because the plurality of X-ray image output apparatus can be controlled one control apparatus, the system can be easily structured or expanded at low cost. Further, because only one control apparatus is sufficient for the plurality of X-ray image output apparatus, the installation area of the control apparatus can be suppressed to the minimum.

(4) An X-ray image radiographing system which comprises: a plurality of X-ray image output apparatus by which, after the X-ray irradiated from the X-ray tube is detected by the detecting means, it is outputted as the digitized image data; a control apparatus to control the plurality of the X-ray image output apparatus; and the X-ray image radiographing system structured by a plurality of communication cables to connect the plurality of X-ray image output apparatus to the control apparatus, wherein the X-ray image radiographing system is structured such that one end of each of the plurality of communication cables is individually connected to each of the plurality of the X-ray image output apparatus and all of the other ends of the plurality of communication cables are connected to the control apparatus, and each of the plurality of the X-ray image output apparatus is individually controlled by the control apparatus through the plurality of communication cables.

According to the invention described in (4), because the system is structured such that one communication cable is allotted to one X-ray image output apparatus, the communication speed between the control apparatus and the X-ray image output apparatus is increased. Further, because it is not necessary that the specification of the communication of the X-ray image output apparatus or the specification of the communication cable to be connected, is common among all of x-ray image output apparatus, the optimum design can be made for respective X-ray image output apparatus. Further, because the plurality of X-ray image output apparatus can be controlled by one control apparatus, the system can be easily structured or expanded at the low cost. Further, because one control apparatus is sufficient for the plurality of X-ray image output apparatus, the installation area of the control apparatus can be suppressed to the minimum.

(5) An X-ray image radiographing system which comprises: a plurality of X-ray tubes; an X-ray generation control apparatus to control the plurality of X-ray tubes; a plurality of X-ray image output apparatus by which, after the X-ray irradiated from each of the plurality of X-ray tubes is detected by the detecting means, it is outputted as the digitized image data; and a control apparatus to control the plurality of the X-ray image output apparatus, wherein each of the plurality of X-ray tubes and each of the plurality of X-ray image output apparatus are controlled by the X-ray generation control apparatus and the control apparatus, according to the predetermined correspondence of the X-ray tube to the X-ray image output apparatus.

According to the invention described in (5), because the X-ray tube and the X-ray image output apparatus are controlled by making them to correspond to each other, the possibility that the operator fails to make the X-ray tube correspond to the X-ray image output apparatus, can be solved. Further, a time to select both of the X-ray tube and the X-ray image output apparatus can be saved. Further, a plurality of X-ray image output apparatus can be controlled by one control apparatus, the system can be easily structured or expanded at the low cost. Further, because one control apparatus is sufficient for the plurality of X-ray image output apparatus, the installation area of the control apparatus can be suppressed to the minimum.

(6) An X-ray image radiographing system which comprises: a plurality of X-ray tubes; an X-ray generation control apparatus to control the plurality of X-ray tubes; a plurality of X-ray image output apparatus by which, after the X-ray irradiated from each of the plurality of X-ray tubes is detected by the detecting means, it is outputted as the digitized image data; and a control apparatus to control the plurality of the X-ray image output apparatus, wherein, when one of the plurality of the X-ray image output apparatus is selected by the control apparatus, the selected X-ray image output apparatus is controlled so that one of the plurality of X-ray tubes corresponding to the selected X-ray image output apparatus is selected by the X-ray generation control apparatus according to the predetermined correspondence, and at a predetermined timing after the X-ray irradiation from the selected X-ray tube, the control apparatus reads out the image data from the selected X-ray image output apparatus.

According to the invention described in (6), because, when one of the plurality of the X-ray image output apparatus is selected, according to the predetermined correspondence, the X-ray tube to be used is automatically selected, a time to select both of the X-ray image output apparatus and the x-ray tube at the time of radiography, can be removed. Further, the possibility that the operator fails to make the X-ray tube correspond to the X-ray image output apparatus, can be solved. Further, because the image data can be automatically obtained from the selected X-ray image output apparatus, the possibility that the operator transmits the image data from the mistaken X-ray image output apparatus, can be removed. Further, because a plurality of X-ray image output apparatus can be controlled by one control apparatus, the system can be easily structured or expanded at the low cost. Further, because one control apparatus is sufficient for the plurality of X-ray image output apparatus, the installation area of the control apparatus can be suppressed to the minimum.

(7) An X-ray image radiographing system which comprises: a plurality of X-ray tubes; an X-ray generation control apparatus to control the plurality of X-ray tubes; a plurality of X-ray image output apparatus by which, after the X-ray irradiated from each of the plurality of X-ray tubes is detected by the detecting means, it is outputted as the digitized image data; and a control apparatus to control the plurality of the X-ray image output apparatus, wherein, when one of the plurality of the X-ray tubes is selected by the X-ray generation control apparatus, one of the plurality of X-ray image output apparatus corresponding to the selected X-ray tube is selected by the control apparatus according to the predetermined correspondence, and the selected X-ray image output apparatus is controlled so that, at a predetermined timing after the X-ray irradiation from the selected X-ray tube, the control apparatus reads out the image data from the selected X-ray image output apparatus.

According to the invention described in (7), because, when one of the plurality of the X-ray tubes is selected, according to the predetermined correspondence, the X-ray image output apparatus to be used is automatically selected, a time to select both of the X-ray image output apparatus and the x-ray tube at the time of radiography, can be removed. Further, the possibility that the operator fails to make the X-ray image output apparatus correspond to the X-ray tube, can be solved. Further, because the image data can be automatically obtained from the automatically selected X-ray image output apparatus, the possibility that the operator transmits the image data from the mistaken X-ray image output apparatus, can be removed. Further, a plurality of X-ray image output apparatus can be controlled by one control apparatus, the system can be easily structured or expanded at the low cost. Further, because one control apparatus is sufficient for the plurality of X-ray image output apparatus, the installation area of the control apparatus can be suppressed to the minimum.

(8) An X-ray image radiographing system which comprises: a plurality of X-ray image output apparatus by which, after the X-ray irradiated from the X-ray tube is detected by the detecting means, it is outputted as the digitized image data; and a control apparatus to control the plurality of the X-ray image output apparatus; and a conditional input means by which any one of the plurality of the X-ray image output apparatus can be selected, wherein, when any one of the plurality of the X-ray image output apparatus is selected, through the conditional input means, the control apparatus controls the selected X-ray image output apparatus so that the image data is read from the selected X-ray image output apparatus.

According to the invention described in (8), because one X-ray image output apparatus can be selected in the plurality of the X-ray image output apparatus by the conditional input means, it is not necessary to prepare the conditional input means or control apparatus for each of the X-ray image output apparatus, and the system can be easily structured or expanded at low cost. Further, because the plurality of the X-ray image output apparatus are satisfied by one of conditional input means or control apparatus respectively, the installation area can be suppressed to the minimum. Further, because the image data can be automatically obtained from the selected X-ray image output apparatus, the possibility that the operator transmits the image data from the mistaken X-ray image output apparatus, is removed.

(9) An X-ray image radiographing system which comprises: a plurality of X-ray image output apparatus by which, after the X-ray irradiated from the X-ray tube is detected by the detecting means, it is outputted as the digitized image data; and a control apparatus to control the plurality of the X-ray image output apparatus; and a display means for displaying the information related to the radiography, wherein, when any one of the plurality of the X-ray image output apparatus is selected, the information which can specify the selected X-ray image output apparatus, or the information which can specify the kind of the selected X-ray image output apparatus, is displayed on the display means, and at a predetermined timing, the control means controls the selected X-ray image output apparatus so that the image data is read from the selected X-ray image output apparatus.

According to the invention described in (9), because, when one the X-ray image output apparatus in the plurality of the X-ray image output apparatus is selected, the information which can specify the selected X-ray image output apparatus, or the kind of the selected X-ray image output apparatus, is displayed on the display means, the selected X-ray image output apparatus can be confirmed again on the display image plane. Thereby, the possibility that the operator photographs by the mistaken X-ray image output apparatus, can be deleted. Further, because a plurality of X-ray image output apparatus can be controlled by one control apparatus, the system can be easily structured or expanded at the low cost. Further, because one control apparatus is sufficient for the plurality of X-ray image output apparatus, the installation area of the control apparatus can be suppressed to the minimum.

(10) An X-ray image radiographing system which comprises: a plurality of X-ray image output apparatus by which, after the X-ray irradiated from the X-ray tube is detected by the detecting means, it is outputted as the digitized image data; and a control apparatus to control the plurality of the X-ray image output apparatus; and a display means for displaying choices of radiographing portion, wherein the choices of the radiographing portion displaying on the display means are determined corresponding to the kind of the X-ray image output apparatus.

According to the invention described in (10), because the choices of the radiographing portion to be displayed are determined corresponding to the kind of the X-ray image output apparatus, the operator can select the objective photographic portion in a short time, without being conscious of the kind of the X-ray image output apparatus when the radiographing portion is selected. Further, because a plurality of X-ray image output apparatus can be controlled by one control apparatus, the system can be easily structured or expanded at the low cost. Further, because one control apparatus is sufficient for the plurality of X-ray image output apparatus, the installation area of the control apparatus can be suppressed to the minimum.

(11) An X-ray image radiographing system which comprises: a plurality of X-ray image output apparatus by which, after the X-ray irradiated from the X-ray tube is detected by the predetermined detecting means, it is outputted as the digitized image data; and a control apparatus to control the plurality of the X-ray image output apparatus; and a display means for displaying choices of radiographing direction, wherein the choices of the radiographing direction displaying on the display means are determined corresponding to a combination of the kind of the X-ray image output apparatus and the radiographing portion.

According to the invention described in (11), because the choices of the radiographing direction to be displayed are determined corresponding to a combination of the kind of the X-ray image output apparatus and the radiographing portion, when the operator selects the radiographing direction, the operator can select the objective photographic direction in a short time, without being conscious of a combination of the kind of the X-ray image output apparatus and the photographic portion. Further, because a plurality of X-ray image output apparatus can be controlled by one control apparatus, the system can be easily structured or expanded at the low cost. Further, because one control apparatus is sufficient for the plurality of X-ray image output apparatus, the installation area of the control apparatus can be suppressed to the minimum.

(12) An X-ray image radiographing system which comprises: a plurality of X-ray image output apparatus by which, after the X-ray irradiated from the X-ray tube is detected by the predetermined detecting means, it is outputted as the digitized image data; and a control apparatus to control the plurality of the X-ray image output apparatus; an image processing means for conducting the predetermined image processing on the image data outputted from the X-ray image output apparatus; and a display means for displaying choices of the radiographing direction, wherein the content of the predetermined image processing conducted by the image processing means, is determined corresponding to any one of a combination of the radiographing portion and the radiographing direction, or a combination of the kind of the detecting means, the radiographing portion and the radiographing direction, or a combination of the kind of the X-ray image output apparatus, the radiographing portion and the radiographing direction.

According to the invention described in (12), because the image processing condition is determined corresponding to any one of a combination of the radiographing portion and the radiographing direction, or a combination of the kind of the detecting means, the radiographing portion and the radiographing direction, or a combination of the kind of the X-ray image output apparatus, the radiographing portion and the radiographing direction, the optimum image processing condition for the kind of the X-ray image processing apparatus or detecting means, the radiographing portion and the radiographing direction, can be automatically determined, and the image data with stable image quality can be always provided. Further, because a plurality of X-ray image output apparatus can be controlled by one control apparatus, the system can be easily structured or expanded at the low cost. Further, because a single control apparatus is sufficient for the plurality of X-ray image output apparatus, the installation area of the control apparatus can be suppressed to the minimum.

(13) The X-ray image radiographing system described in any one of items (1) to (12), wherein, in the plurality of X-ray image output apparatus, the information by which the X-ray image output apparatus outputted the image data, can be specified, or the kind of X-ray image output apparatus which outputted the image data, can be specified, is made to correspond to the image data and stored.

According to the invention described in (13), because the information by which the X-ray image output apparatus used in the radiographing or its kind can be specified, is made to correspond to the image data and stored, even after a long period of time has passed, the X-ray image output apparatus used for radiography can be specified at once. Specifically, in the case where the person except the operator refers to the image data, when the person discovers any failure in the image data, there is a merit that, by which X-ray image output apparatus the image data is radiographed, can be specified soon.

(14) The X-ray image radiographing system described in any one of items (1) to (12), wherein at least one of the plurality of X-ray image output apparatus is a stand alone type X-ray image output apparatus whose detecting means is a solid state plane detector or a stimulative fluorescent substance, and at least one of the plurality of X-ray image output apparatus is a lying type X-ray image output apparatus whose detecting means is a solid state plane detector or a stimulative fluorescent substance.

According to the invention described in (14), because a plurality of X-ray image output apparatus can be controlled by one control apparatus, without depending on the detecting means or type of the system, the operator can easily structure or expand the system at low cost.

(15) The X-ray image radiographing system described in any one item of items (1) to (4), and items (7) to (12), wherein the detecting means is a stimulative fluorescent substance plate housed in the portable type cassette, and the plurality of X-ray image output apparatus is a cassette correspondent type X-ray image output apparatus having a reading means for reading the X-ray image information from the stimulative fluorescent substance plate housed in the portable type cassette.

According to the invention described in (15), even when a plurality of sets of the cassette corespondent X-ray image output apparatus using the stimulative fluorescent substance plate are used, because these can be controlled by one control apparatus, only the X-ray image output apparatus can be increased or decreased corresponding to the radiographing frequency of the facility. Accordingly, the system can be easily structured or expanded at low cost.

(16) The X-ray image radiographing system described in any one item of items (1) to (12), wherein at least one of the plurality of X-ray image output apparatus is a stand alone type or lying type X-ray image output apparatus whose detecting means is a solid state plane detector or a stimulative fluorescent substance, and at least one of the plurality of X-ray image output apparatus is a cassette correspondent type X-ray image output apparatus having the reading means for reading the X-ray image information from the stimulative fluorescent substance plate housed in the portable type cassette.

According to the invention described in (16), because an exclusive use type (stand alone type or lying type) and the cassette correspondent type X-ray image output apparatus can be controlled by one control apparatus, the system can be easily structured or expanded at low cost, without the operator being limited by the detecting means or the type of the system.

(17) An X-ray image radiographing system which comprises: an X-ray image output apparatus by which, after the X-ray irradiated from the X-ray tube is detected by the detecting means, it is outputted as the digitized image data; and a control apparatus to control the X-ray image output apparatus; and a display means for displaying choices of radiographing direction; and a condition input means which can select or/and decide a specific radiographing direction from the choice of the radiographing direction displayed on the display means, wherein, in the choice of the radiographing direction displayed on the display means, the choice to select a plurality of radiographing directions at a time is included, and when, after the choice to select a plurality of radiographing directions at a time is selected by the condition input means, it is decided, the plurality of radiographing directions corresponding to the selected and decided choice are registered in the control apparatus.

According to the invention described in (17), because the choice which can select the plurality of radiographing directions at a time, is provided in the choice to select the radiographing direction, a time to individually select the plurality of radiographing directions, can be saved, and the selection of the radiographing direction can be completed in a short time.

(18) An X-ray image radiographing system which comprises: an X-ray image output apparatus by which, after the X-ray irradiated from the X-ray tube is detected by the detecting means, it is outputted as the digitized image data; and a control apparatus to control the X-ray image output apparatus; and a display means for displaying choices of radiographing position or radiographing direction; and a condition input means which can select a specific radiographing region or radiographing direction from the choice of the radiographing region or radiographing direction displayed on the display means, wherein, when a plurality of the radiographing regions or radiographing directions are selected from the choice of the radiographing region or radiographing direction displayed on the display means, through the condition input means, the content of the plurality of the radiographing regions or radiographing directions is successively displayed on the display means.

According to the invention described in (18), because the content of the selected plurality of the radiographing regions or radiographing directions is successively displayed on the display means, the operator can operate while confirming always the selected content, thereby, the mistake of the operation of the operator can be prevented.

(19) The X-ray image radiographing system described in (18), wherein the system has a function to erase the content of the radiographing regions or radiographing directions successively displayed on the display means.

According to the invention described in (19), because the content of the selected plural radiographing regions or radiographing directions is successively displayed on the display image plane, and the displayed content can be erased, even when the operator mistakes the selection, the input can be simply erased. Thereby, the efficiency of the operability can be increased.

(20) The X-ray image radiographing system described in (18), wherein the system has a function to modify the content of the radiographing regions or radiographing directions successively displayed on the display means.

According to the invention described in (20), because the content of the selected plurality of radiographing regions or radiographing directions is successively displayed on the display means, and the displayed content can be modified, even when the operator mistakes the selection, the input can be simply modified. Thereby, the efficiency of the operability can be increased.

(21) The X-ray image radiographing system described in (18), wherein the system has a function to decide the content of the radiographing regions or radiographing directions successively displayed on the display means.

According to the invention described in (21), because the content of the selected plurality of radiographing regions or radiographing directions is successively displayed on the display image plane, and a function to decide the displayed content is added thereto, the operator confirms again the selected content, and can decide the selected content. Thereby, the reliability of the operation and the safety of the radiography can be increased.

(22) An X-ray image radiographing system which comprises: an X-ray image output apparatus by which, after the X-ray irradiated from the X-ray tube is detected by the detecting means, it is outputted as the digitized image data; and a control apparatus to control the X-ray image output apparatus; and an image processing means for conducting the predetermined image processing on the image data outputted from the X-ray image output apparatus, wherein, when a pixel value of the image data outputted from the X-ray image output apparatus is the image data which is almost linear to the X-ray intensity, after the image processing means conducts the logarithmic conversion on the image data, the predetermined image processing is conducted, and when the pixel value of the image data outputted from the X-ray image output apparatus is the image data which is almost linear to the logarithm of the X-ray intensity, the image processing means does not conducts the logarithmic conversion on the image data, but the predetermined image processing is conducted.

According to the invention described in (22), because, even when any one of the X-ray image output apparatus to output the image data almost linear to the X-ray intensity, and the X-ray image output apparatus to output the image data almost linear to the logarithm of the X-ray intensity, is connected to the control apparatus, the processing can be conducted by the same image processing means, a widely usable system can be structured without being influenced by the data type of the image data.

(23) An X-ray image radiographing system which comprises: an X-ray image output apparatus by which, after the X-ray irradiated from the X-ray tube is detected by the detecting means, it is outputted as the digitized image data; and a control apparatus to control the X-ray image output apparatus; and an image processing means for conducting the predetermined image processing on the image data outputted from the X-ray image output apparatus, wherein, after different correction processing is conducted corresponding to the kind of the detecting means, the predetermined image processing is conducted by the image processing means.

According to the invention described in (23), because, after different correction processing is conducted corresponding to the kind of the detecting means, the predetermined image processing is conducted, a widely usable system can be structured without being influenced by the kind of the detecting means.

(24) The X-ray image radiographing system described in any one item of items (22) and (23), wherein at least one of the predetermined image processing conducted by the image processing means is the gradation conversion processing.

According to the invention described in (24), because, after the difference of the kind of the detecting means or the difference of the data type of the image data is corrected, the gradation conversion processing is conducted, the image data with the stable gradation characteristic, which is not influenced by the difference of the kind of the detecting means or the difference of the data type of the image data, can be provided.

(25) The X-ray image radiographing system described in any one item of items (22) and (23), wherein the content of the predetermined image processing conducted by the image processing means is constant without depending on the kind of the detecting means.

According to the invention described in (25), because the constant image processing can be conducted by the image processing means without depending on the kind of the detecting means, a processing program of the image processing becomes easy, and the development cost of the processing program can be decreased, and the storage capacity necessary for storing the processing programs or processing parameters can be decreased.

(26) The X-ray image radiographing system described in any one item of items (22) and (23), wherein a part of the content of the predetermined image processing conducted by the image processing means is different depending on the kind of the detecting means.

According to the invention described in (26), because a part of the content of the predetermined image processing conducted by the image processing means is changed depending on the kind of the detecting means, the image processing to decrease the difference of the kinds of the detecting means to the minimum, can be conducted corresponding to the kind of the detecting means.

(27) The X-ray image radiographing system described in any one item of items (12) or (25) to (26), wherein the predetermined image processing conducted by the image processing means is at least one of the gradation conversion processing, frequency processing, and dynamic range compression processing.

According to the invention described in (27), because, for the item (12), the processing content of the gradation conversion processing, frequency processing, and dynamic range compression processing can be optimized corresponding to a combination of the kind of the detecting means, the kind of the X-ray image output apparatus, radiographing region, and photographic direction, the image data with the highest image quality can be always stably supplied. Further, for the items (25) and (26), because the image processing conducted by the image processing means is at least one of the gradation conversion processing, frequency processing, and dynamic range compression processing, the optimum image processing can be selected corresponding to the request of the operator.

(28) The X-ray image radiographing system described in item (23), wherein the content of the correction processing includes at least one of the gain correction and the offset correction when the detecting means is a solid state plane detector, and when the detecting means is the stimulative fluorescent substance, at least one of a surface falling correction of a polygonal mirror used for the laser scanning means, a correction of the unevenness generated in the light conversing means for conversing the stimulation light, a correction of the uneven sensitivity proper to the stimulative fluorescent substance, and a correction of uneven sub-scanning generated in a conveying means.

According to the invention described in (28), because, after the correction processing corresponding to the kind of the detecting means, the image processing can be conducted, the finish of the image processing is increased, and the image data desirable for the operator can be provided. Further, because the correction processing is structured such that it can correspond to both of detecting means of the solid state plane detector and the stimulative fluorescent substance, the flexible system can be structured without depending on any means.

(29) The X-ray image radiographing system described in item (23), wherein the content of the correction processing includes at least one of the correction of the resolution of the image data, the correction of the density resolving power of the image data, and the correction of the number of bits per one pixel of the image data.

According to the invention described in (29), because the image processing can be conducted after the attribute of the image data depending on the kind of the detecting means is corrected, the stable image quality not depending on the difference of the kind of the detecting means can be provided.

(30) The X-ray image radiographing system described in item (23), (28), or (29), wherein the content of the correction processing is stored by being made correspondence to the image data.

According to the invention described in (30), because the content of the correction processing is stored by being made correspondence to the image data, the operator can confirm the content of the correction processing conducted on the image data after a time, and when any problem is found, the operator can cope with it soon.

(31) An X-ray image radiographing system which comprises: an X-ray image output apparatus by which, after the X-ray irradiated from the X-ray tube is detected by the detecting means, it is outputted as the digitized image data; and a control apparatus to control the X-ray image output apparatus; and the image processing means for conducting the predetermined image processing on the image data outputted from the X-ray image output apparatus, wherein the difference of the characteristic of the image data generated by the difference of the detecting means or the difference of the operation of the X-ray image output apparatus is made a parameter, and the image processing means conducts the predetermined image processing according to the parameter.

According to the invention described in (31), because the difference of the characteristic of the image data generated by the difference of the detecting means is absorbed by the parameter of the image processing, the image processing can be conducted by using the same image processing program without depending on the difference of the detecting means or the difference of the operation of the X-ray image output apparatus. Thereby, the image data with the always stable image quality can be provided without depending on the difference of the detecting means or the difference of the operation of the X-ray image output apparatus, and a widely usable system can be structured without being influenced by the difference of the detecting means or the difference of the operation of the X-ray image output apparatus.

(32) The X-ray image radiographing system described in item (31), wherein the parameter is at least one of a parameter relating to the resolution of the image data, a parameter relating to the density resolving power of the image data, and a parameter relating to the number of bits per one pixel of the image data.

According to the invention described in (32), because, even when the resolution of the image data, density resolving power, or the number of bits per 1 pixel, is different, the unified image processing can be conducted, the stable image quality not depending on the difference of the detecting means, or the difference of the operation of the X-ray image output apparatus, can be provided.

(33) The X-ray image radiographing system described in item (31), or (32), wherein the content of the parameter is stored by being made to correspond to the image data.

According to the invention described in (32), because the content of the parameter is stored by being made to correspond to the image data, the operator can conform under which condition the image processing is conducted, after a time, and when any problems is found, the operator can cope with it soon.

(34) The X-ray image radiographing system described in item (31), or (32), wherein the predetermined image processing conducted by the image processing means is at least one of the gradation conversion processing, frequency processing, and dynamic range compression processing.

According to the invention described in (34), because the image processing conducted by the image processing means is at least one of the gradation conversion processing, frequency processing, and dynamic range compression processing, the optimum image processing can be selected corresponding to the request of the operator.

(35) The X-ray image radiographing system described in items (22), (23) or (31), wherein the detecting means is the solid state plane detector or the stimulative fluorescent substance.

According to the invention described in (35), because the detecting means corresponds to the solid state plane detector or the stimulative fluorescent substance, the stable image quality can be provided to the X-ray image output apparatus using the solid state plane detector or the X-ray image output apparatus using the stimulative fluorescent substance.

(36) An X-ray image radiographing system which comprises: an X-ray image output apparatus by which, after the X-ray irradiated from the X-ray tube is detected by the detecting means, it is outputted as the digitized image data; and a control apparatus to control the X-ray image output apparatus; and a display means for displaying the image information of the image data, wherein the X-ray image radiographing system has the first display image plane to display the image data finally outputted from the X-ray image output apparatus, the second display image plane to display at least one of a patient name, patient ID number, radiographing region, corresponding to the image data displayed on the first display image plane, and radiographing direction, and the third display image plane to reduction-display a plurality of image data outputted from the X-ray image output apparatus before the image data displayed on the first display image plane.

According to the invention described in (36), because the operator can refer to and confirm the past radiography which is formed into an image, the reliability of referring and confirming operation to the past radiography and the operation efficiency can be increased.

(37) The X-ray image radiographing system described in item (36), wherein the plurality of reduced image data displayed on the third display image plane is displayed in a time series to the time of any one of (1) a time at which the X-ray radiographing system receives the reserve registration of the radiography, or its equivalent time, (2) a time at which the X-ray is irradiated onto the object, or its equivalent time, (3) a time at which the image data is generated in the X-ray image output apparatus, or its equivalent time, and (4) a time at which the control apparatus receives the image data, or its equivalent time.

According to the invention described in (37), because the operator can refer to or confirm the past radiography by forming it into an image, according to the time series such as the radiographing time, the reliability of the referring and confirming operation to the past radiography and the operation efficiency can be more increased.

(38) The X-ray image radiographing system described in item (36) or (37), wherein the plurality of reduction image data displayed on the third display image plane are the image data of the same patient.

According to the invention described in (38), because only the image of the same patient is formed into the image and referred to and confirmed, the possibility that the image is confused with the image of another patient, is removed, and the reliability of the referring and confirming operation and the safety can be increased.

(39) The X-ray image radiographing system described in any one of items (36) to (38), wherein the system has a function which can select an arbitrary reduction image data in the plurality of reduction image data displayed on the display image plane, and when an arbitrary reduction image data in the plurality of reduction image data is selected by the function which can select an arbitrary reduction image data, the selected reduction image data is enlarged and displayed.

According to the invention described in (39), because the image of the patient radiographed in the past time is enlarged and displayed, the referring and confirming operation of the past image can be conducted by using the finer image information, thereby, the reliability of the referring and confirming operation and the operation efficiency can be further increased.

(40) The X-ray image radiographing system described in item (22) or (36), wherein the detecting means is a solid state plane detector or stimulative fluorescent substance.

According to the invention described in (40), because the system corresponds to the solid state plane detector or stimulative fluorescent substance, the highly reliable and efficient referring and confirming operation can be conducted on the X-ray image output apparatus using the solid state plane detector, or the X-ray image output apparatus using the stimulative fluorescent substance.

DETAILED DESCRIPTION OF THE PREFERRED EMBODIMENT

Figure 1:
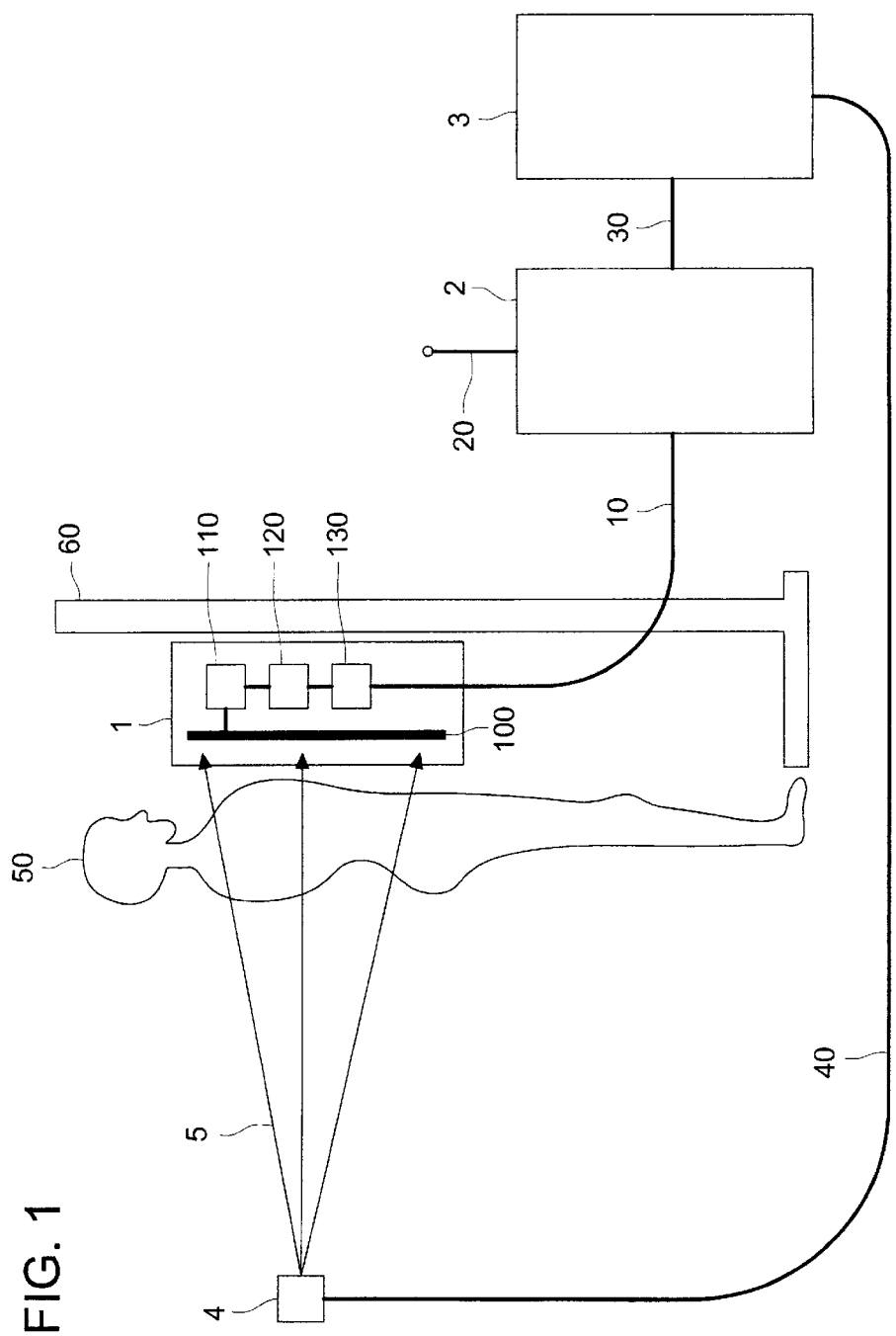
FIG. 1 is a view showing a structural example of a stand alone type X-ray image radiographing system.

An embodiment of an X-ray image radiographing system of the present invention will be described below. Initially, referring to FIG. 1, FIG. 2 and FIG. 3, an operation of an individual system forming a minimum unit of the X-ray image radiographing system which is the present invention, will be described below.

Initially, an exclusive use type X-ray image radiographing system will be described by using FIG. 1 and FIG. 2. Because a stand alone type X-ray image radiographing system shown in FIG. 1 and also a lying type X-ray image radiographing system shown in FIG. 2 have the similar operation, these will be described at one time.

When an X-ray generation control apparatus 3 is operated and an X-ray 5 is irradiated from an X-ray tube 4 onto a subject 50, the X-ray transmitted through the subject 50 is detected by a detecting means 100. Because a portion of the irradiated X-ray 5 is absorbed by the subject 50, the X-ray detected by the detecting means 100 can be regarded as the X-ray image information reflecting an X absorption distribution of the subject 50.

The X-ray image information detected by the detecting means 100 is read out by a reading means 110 as an electric signal, by the instruction of a control apparatus 2, and digitized by an AD converting means 120. Hereinafter, the digitized X-ray image information is called the image data. The image data generated by the AD converting means 120 is transferred to the control apparatus 2 through a communication means 130 and a communication cable 10.

Such a series of main operations of the X-ray image output apparatus 1, are controlled by the control apparatus 2 through the communication cable 10. The control apparatus 2 is connected to an X-ray generation control apparatus 3 which controls the generation of the X-ray, through a communication cable 30.

The generation timing of the X-ray 5 is noticed from the X-ray generation control apparatus 3 to the control apparatus 2 through the communication cable 30. The control apparatus 2 is in timed relationship with the noticed X-ray generation timing and instructs the reading out of the image data to the X-ray image output apparatus 1.

Next, the cassette correspondent type X-ray image radiographing system will be described by using FIG. 3. In the case of this example, the detecting means 100 is a stimulative fluorescent substance plate.

A cassette 6 is held to a concerning portion (a portion desired to conduct the X-ray radiography) of the subject 50, and the X-ray generation control apparatus 3 is operated and the X-ray 5 is irradiated from the X-ray tube 4. The X-ray energy transmitted through the subject 50 is detected by the detecting means 100 housed in the cassette 6, and after that, it is temporarily accumulated and held inside the stimulative fluorescent substance plate which is the detecting means 100.

After the X-ray radiographing is completed, when the cassette 6 is inserted into the X-ray image output apparatus 1 having a reading means 110, the X-ray image output apparatus 1 pulls out the detecting means 100 from the cassette 6, and while the detecting means 100, that is, the stimulative fluorescent substance plate is being sub-scanning conveyed in the direction of A by a conveying means 90, the X-ray image information accumulated and held in the detecting means 100 is read out by the reading means 110.

The reading means 110 is composed of a laser scanning means 111, converging means 112, and a photoelectric conversion means 113. While the detecting means 100 is sub-scanning conveyed by the conveying means 90, the laser scanning means 111 scans the laser light 114 in the direction (main-scanning direction) perpendicular to the sub-scanning direction.

When the laser light acts onto the stimulative fluorescent substance plate which is the detecting means 100, the energy accumulated inside the fluorescent substance is generated as the stimulation light 115. The energy released as the stimulation light has an energy amount proportional to the X-ray energy amount detected by the detecting means 100. This stimulation light 115 is converged by the converging means 112, and the converged stimulation light 115 is taken out as an electric signal by a photoelectric conversion means 113 such as a photo-multiplier.

The stimulation light 115 read out as the electric signal by the reading means 110 is digitized by the AD conversion means 120, and the image data is generated. The image data generated by the AD conversion means 120 is transmitted to the control apparatus 2 by the communication means 130 through the communication cable 10.

Such a series of main operations of the X-ray image output apparatus 1 is controlled by the control apparatus 2 through the communication cable 10.

In the cassette correspondent type X-ray image radiographing system, it is net necessary that the irradiation time of the X-ray 5 from the X-ray tube 4 onto the subject 50, or the detection time of the X-ray image information by the detecting means 100 is in timed relationship with the reading-out time of the X-ray image information by the reading-out means 110.

Figure 4:
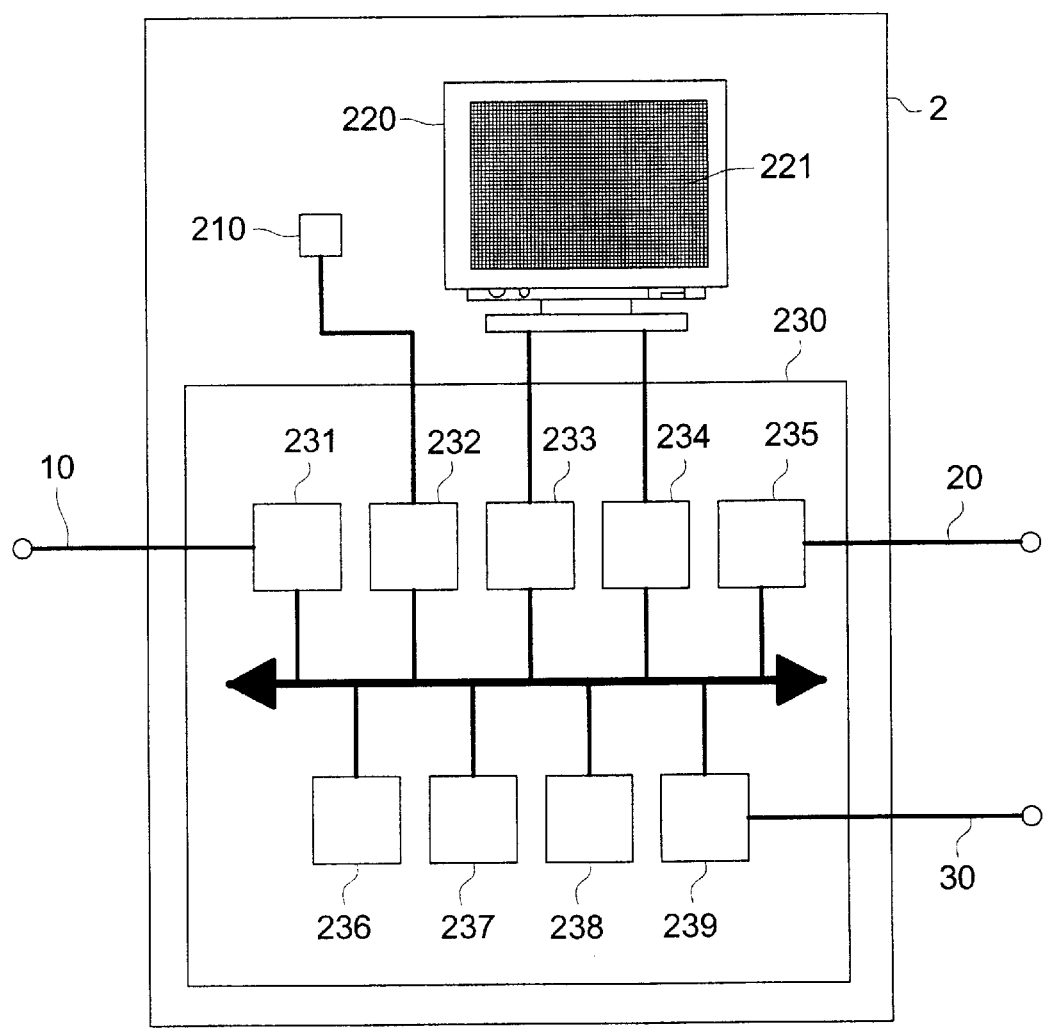
FIG. 4 is a view showing a structural example of a control apparatus.

FIG. 4 is a view for further detailing the control apparatus 2 which is a part of the present invention. The control apparatus 2 is composed of a patient information input means 210, display means 220, conditional input means 221, and control unit 230.

The control unit 230 is structured by: a communication means 231 for obtaining the image data from the X-ray image output apparatus 1 through the communication cable 10, or for transmitting the control signal to the X-ray image output apparatus 1; a patient information input control means 232 for controlling the patient information input means 210; a display control means 233 for control the display means 220; a conditional input control means 234 for controlling the conditional input means 221; a communication means 235 for outputting the image data or the information contingent to the image data through the communication cable 20 to the outside; a control means 236 for controlling each means inside the control means 2 or the X-ray image output apparatus 1; an image processing means 237 for processing the image data received from the X-ray image output apparatus 1; a storage means 238 for storing the image data, or the information contingent to the image data, and the patient information; and a communication means 239 which is a means for communicating with the X-ray generation control apparatus 3 through the communication cable 30.

The patient information input means 210 is a means for inputting the patient information of a patient to be radiographed, and for example, when the patient information input means 210 is connected to the hospital information system (HIS) or radioactive ray information system (RIS), it can receive the patient information from these HIS or RIS. In this case, the information relating to the radiography such as the radiographing region or radiographing direction can also be taken in the control apparatus 2 through the patient information input means 210.

Further, the patient information input means 210 may be a bar code reader. In this case, the patient information is expressed by the bar code, and by the bar code reader which is the patient information input means 210, the patient information which is formed into the bar code, is read out.

Further, the patient information input means 210 may be a magnetic card reader or an IC card reader. In this case, the patient information is stored in the magnetic card or IC card, and the patient information stored in the magnetic card or IC card is read out by the magnetic card reader or an IC card reader, which is the patient information input means 210.

Further, the patient information input means 210 may be a key board. In this case, the operator inputs the patient information by using the key board.

Further, the patient information input means 210 may be an apparatus for inputting the voice. In this case, the operator inputs the patient information by the voice. The patient information is, for example, the name of the patient, the date of the birth of the patient, the distinction of sex, address, ID number, and the date of radiography. the patient information inputted by the patient information input means 210 is temporarily stored in the storage means 238.

The display means 220 is, for example, a means which can display the character information or the image information, such as a CRT display, or liquid crystal display, and displays the patient information, photographic sensitivity information, the kind of the radiographing apparatus, the radiographing region, radiographing direction, X-ray radiographing condition obtained from the X-ray generation control apparatus 3, the information to specify the X-ray image output apparatus which obtained the image data, the resolution of the image data or sampling pitch, the number of pixels of the image data, the number of bits pert one pixel of the image data, the kind of the image processing, the image processing parameter, the information of the content of the correction processing (hereinafter, these information are collectively called the image data-attached information), and an image of the radiographed image data. The content of the display is controlled by the display control means 233. The operator can confirm the name of the patient or radiographing region by the information displayed on the display means 220 before the radiography. Further, after the radiography, by looking at the image of the image data displayed on the display means 220, the operator can confirm the good or bad of the radiography.

As the conditional input means 221, although a touch panel is assumed in FIG. 4, it may be another means, for example, a key-board, mouse, track ball, or voice input apparatus. When the conditional information which is necessary for the operator, is selected from the image data-attached information through the conditional input means 221, the selected conditional information is inputted into the inside of the control unit 230 through the input control means 234, and registered. Further, the already inputted conditional information can be changed and deleted by operating the conditional input means 221.

For example, a list of the radiographing regions is displayed on the display means 220 as a plurality of icons, and when the operator touches (selects) to one of icons, the radiographing region corresponding to the touched (selected) icon is stored (registered) in the storage means 237 as the image data-attached information.

The communication means 231 is a means for conducting the communication with the X-ray image output apparatus 1 through the communication cable 10. The content of the communication is the control information of the X-ray image output apparatus 1, the information to specify the X-ray image output apparatus, the image data outputted from the X-ray image output apparatus 1, and the correction data used for correcting the image data. The image data or correction data received by the communication means 231 is stored in the storage means 238. The communication means 231 can be increased corresponding to the number of the X-ray image output apparatus 1 having the connectivity or the connection method.

The image processing means 237 is a means for conducting the predetermined image processing for the image data received by the communication means 231. As the kinds of the image processing, there exists the gradation conversion processing to convert the gradation possessed by the image data, the frequency processing to convert the frequency characteristic of the image data, or the dynamic range compression processing to compress the dynamic range of the image data.

Specifically, in the gradation conversion processing, in order to obtain the gradation characteristic as in the case of the radiography by the screen/film system, the processing in which the gradation characteristic of the image data which is linear to the logarithm of the X-ray intensity is converted into the gradation characteristic which is nonlinear to the logarithm of the X-ray intensity, is used the most. Because it is desirable that the image processing such as the gradation conversion processing, frequency processing, or the dynamic range compression processing, is conducted for the image data which is linear to the logarithm of the X-ray intensity, in the present invention, when the image data outputted from the X-ray image output apparatus 1 is the data almost linear to the X-ray intensity, before the image processing is conducted, the processing which conducts the logarithmic conversion is automatically conducted.

For example, when the X-ray image output apparatus 1 is an apparatus using the solid state plane detector, because, generally, there are many cases in which the image data almost linear to the X-ray. intensity is outputted, in such the case, it is controlled such that the logarithmic conversion is automatically conducted on the image data.

On the one hand, when the X-ray image output apparatus 1 is an apparatus using the stimulative fluorescent substance, generally, because the image data almost linear to the logarithm of the X-ray intensity is outputted, in such the case, it is controlled such that the logarithmic conversion processing is not conducted on the image data.

As described above, in the present invention, because the system is structured such that the logarithmic conversion processing is automatically conducted on the image data almost linear to the X-ray intensity, even when any one of the X-ray image output apparatus outputting the image data almost linear to the X-ray intensity, and the X-ray image output apparatus outputting the image data almost linear to the logarithm of the X-ray intensity is used, the image processing can be conducted by the same image processing means 237.

When the kind or content (the degree of the processing) of the image processing processed by the image processing means 237 is made the same in the case of the apparatus using the solid state plane detector and the case of the apparatus using the stimulative fluorescent substance, the processing program becomes simple, and the development cost can be reduced. Further, the storage capacity necessary for storing the processing program or processing parameter can be reduced.

Further, the kind or content (the degree of the processing) of the image processing processed by the image processing means 237 may be different from each other in the case of the apparatus using the solid state plane detector and the case of the apparatus using the stimulative fluorescent substance. This is because the detecting means is different from each other in the solid state plane detector and the stimulative fluorescent substance, and the frequency or gradation characteristic of the image data is delicately different. Accordingly, corresponding to the difference between the detecting means, by changing the kind of the image processing, or by changing the content·degree even in the case of the same image processing, these can be finished to the image data in which the difference between the different detectors is not conspicuous.

For the purpose that the result of the image processing conducted by the image processing means 237 is satisfactory, it is preferable that, before the image processing is conducted, the correction processing to correct the unevenness specific to the detecting means 100 and the reading means 110 is conducted. The correction processing may be conducted by the image processing means 237, or in the inside of the X-ray image output apparatus 1.

As the correction processing when the detecting means 100 is the solid state plane detector, there are a gain correction and an offset correction. The offset correction processing is a processing to correct the fluctuation in the implied output voltage of the solid state plane detector or fluctuation in the reading-out amplifier noise. On the one hand, the gain correction is a processing to correct the sensitivity unevenness of the solid state plane detector or the gain unevenness of the reading-out amplifier.

When x is a pixel position of the data, the image data before the correction is expressed as f(x), the gain correction data is expressed as p(x), and the offset correction data is expressed as q(x), the image data after gain correction and offset correction is expressed as the following:

$$F(x)=\{f(x)-q(x)\}*p(x) \qquad (1)$$

Further, when only the offset correction is necessary, it is expressed as the following:

$$F(x)=f(x)-q(x) \qquad (2)$$

Further, when only the gain correction is necessary, it is expressed as the following:

$$F(x)=f(x)*p(x) \qquad (3)$$

Herein, the image data f(x) before the correction, the image data F(x) after the correction, the gain correction data p(x), and the offset correction data q(x) are all the data linear to the X-ray intensity.

On the one hand, the correction processing when the detecting means 100 is the stimulative fluorescent substance, is the surface fall-down correction processing of the polygonal mirror used in the laser scanning means 111, the correction processing of the unevenness generated in the converging means 112 for converging the stimulation light, the correction processing of the sensitivity unevenness specific to the stimulative fluorescent substance, or the correction processing of the sub-scanning unevenness generated in the conveying means 90.

When x is a pixel position of the data, the image data before the correction is expressed by g(x), the image data after the correction is expressed by G(x), and the correction data is expressed by h(x), then, the image data after the correction is expressed by $$G(x)=g(x)\pm h(x) \qquad (4).$$

Herein, the image data g(x) before the correction, the image data G(x) after the correction, and the correction data h(x) are all the data linear to the logarithm of the X-ray intensity.

In the present invention, because the image processing is conducted after the correction processing corresponding to the kind of the detecting means 100 as described above is conducted, the finish of the image processing is improved, and the image data with the fine image quality can be obtained.

It is well known that, depending on the difference of the detecting means 100, or the difference of the operation of the X-ray image output apparatus 1, the resolution which is an attribute of the image data, density resolving power, and the number of bits per one pixel, are different. Generally, in the apparatus processing the X-ray image, because the image processing is designed under the presupposition of the use of a specific detecting means, when the fluctuation is generated in the attribute of the image data, the normal image processing can not be conducted.

For example, in the case where a predetermined frequency processing is conducted on the image data, when the resolution of the image data is different, because the emphasized or depressed frequency component or frequency band is different, a disadvantage that the finish of the image is different, is generated.

In the present invention, in order to solve these problems, the following 2 methods are provided.

Initially, the first method is a method in which: the reference value of the attribute of the image data is decided; and when the attribute of the obtained image data is different from the reference value, the image data itself is deformed (the correction processing is conducted on the image data itself); and the attribute of the image data is made to coincide with the reference value. For example, in the case where the reference value of the bit number per one pixel is 12 bits, when the bit number per one pixel of the obtained image data is 14 bits, the processing by which the lower 2 bits of the obtained image data are discarded, and the image data is forcibly made to 12 bit data, is conducted.

As described above, the obtained image data itself is deformed, and the attribute of the image is forcibly made to coincide with the reference value, and the image processing is conducted by the image processing means 237. Because the attribute of the image data is made to coincide with the reference value, the image processing can be conducted without raising any problem. The second method is a method in which: the image data is not made to coincide with the reference value; and the fluctuation of the attribute of the image data generated by the difference of the detecting means 100 or the difference of the operation of the X-ray image output apparatus 1 is absorbed by the program of the image processing. That is, the image processing program to allow the fluctuation of the attribute of the image data is designed, and before the image processing is conducted, the attribute of the image data is delivered to the image processing program as the parameter.

For example, when the bit number per one pixel of the image data is 14 bits, the parameter showing that the bit number per one pixel is 14 bits, is delivered to the image processing program. The image processing program recognizes that, for example, the maximum value to the inputted image data is 16383 in the decimal number, and conducts the predetermined image processing program on the image data.

In this manner, when the image processing is conducted, because the fluctuation in the attribute of the image data can be absorbed in the inside of the image processing program, the image processing can be conducted without raising the problem.

In the present invention, because the content of the various correction processing described above, the kind of the image processing, and the image processing parameter, are made to correspond to the image data as the image data-attached information, and stored in the storage means 238, the operator can confirm later the content of the correction processing or image processing conducted on the image data.

The storage means 238 is a means for storing the image data, correction data, or image data-attached information temporarily or for a long period. It is preferable that both of the image data before the image processing, and the image data after the image processing are stored as the image data.

The communication means 239 is a means for communicating with the X-ray generation control apparatus 1 through the communication cable 30. The content of the communication is the information relating to the timing of the X-ray irradiation, or the X-ray radiographing condition. The X-ray radiographing condition is the information such as the X-ray irradiation time, the current value flowing through the X-ray tube, and the tube voltage of the X-ray tube, or when a plurality of X-ray tubes exist, the information showing which X-ray tube is selected.

The information relating to the timing of the X-ray irradiation is important in the case of the exclusive use type X-ray image radiographing system, or in the case of the cassette correspondent type X-ray image radiographing system using the plane detector.

In the X-ray image radiographing system in which such the X-ray irradiation timing is important, the timing at which the reading-out means 110 in the X-ray image output apparatus 1 reads out the image data from the detecting means 100, is made in the control means 236 based on the timing of the irradiation of the X-ray received from the X-ray generation control apparatus 1.

The communication means 235 is connected to the network inside the hospital by the communication cable 20, and outputs the image data or the other information to various apparatus, for example, a viewing system in which the image data is displayed on the CRT and the diagnosis is conducted, the image data archiver to store the image data for a long period of time, a dry imager to film-output the image data, or an ink-jet printer.

Next, by using FIG. 5, an embodiment of the X-ray image radiographing system which is the present invention, that is, an embodiment of the exclusive-use type X-ray image radiographing system will be described. In the present example, 3 X-ray image output apparatus 1a, 1b, and 1c are successively connected onto the communication cable 10.

In the X-ray radiographing room, the installation position of the X-ray image output apparatus 1a, 1b, and 1c and the installation position of the control apparatus 2 are separated as far as possible so that the operator is not exposed by the X-ray. That is, in many cases, the communication cable length between the control apparatus 2 and the X-ray image output apparatus 1a is longer than the communication cable length between the X-ray image output apparatus 1a and the X-ray image output apparatus 1b, or the communication cable length between the X-ray image output apparatus 1b and the X-ray image output apparatus 1c.

Accordingly, when the system is structured such that the X-ray image output apparatus 1a, 1b and 1c are successively connected onto the communication cable 10, the total cable length of the communication cable can be reduced, and the apparatus cost can be reduced. Further, the interface substrate constituting the communication means 231 on the control apparatus 2 side can be structured by one substrate, and the apparatus cost is further reduced. Further, because the system may control the interface of one system, the communication control program of the control means 236 can be simplified, and the development cost and the development load can be decreased. The X-ray image output apparatus 1a, 1b, and 1c are controlled by one control apparatus 2 through the communication cable 10. The control apparatus 2 controls 3 X-ray image output apparatus 1a, 1b, and 1c, for example, by ID numbers.

The present example is an example in which one control apparatus 2 controls 3 X-ray image output apparatus 1a, 1b, and 1c, however, the present invention does not limit the number of X-ray image output apparatus controlled by the control apparatus 2. Respective of 3 X-ray image output apparatus 1a, 1b, and 1c are exclusive-use type X-ray image output apparatus in the present example, and may be any one of the stand alone type or lying type one.

Respective detecting means 100 of 3 X-ray image output apparatus 1a, 1b, and 1c may be the solid state plane detector, or stimulative fluorescent substance, or other X-ray detecting means.

Three X-ray tubes 4a, 4b, and 4c are connected through the cable 40 to the X-ray generation control apparatus 3, connected to the control apparatus 2 through the communication cable 30, and the X-ray tubes 4a, 4b and 4c are made to respectively correspond to the X-ray image output apparatus 1a, 1b, and 1c. That is, the system is controlled in such a manner that, when the radiographing is conducted by the X-ray image output apparatus 1a, the X-ray tube 4a is used, when the radiographing is conducted by the X-ray image output apparatus 1b, the X-ray tube 4b is used, and when the radiographing is conducted by the X-ray image output apparatus 1c, the X-ray tube 4c is used.

The present example is an example in which the X-ray tube and the X-ray image output apparatus are made to correspond to each other 1 to 1, however, for example, even when the X-ray tube 4c does not exist, and the X-ray tube 4b is made to correspond to the X-ray image output apparatus 1b and 1c, it may be allowable. That is, the system may be structured such that one X-ray tube is made to correspond to more than 2 X-ray image output apparatus.

In this case, when the radiography by the X-ray image output apparatus 1a is instructed, the system is controlled such that the X-ray tube 4a is used, and when the radiography by the X-ray image output apparatus 1b or the X-ray image output apparatus 1c is instructed, the system is controlled such that the X-ray tube 4b is used.

When one of 3 X-ray tubes 4a, 4b and 4c is selected by the X-ray generation control apparatus 3, the information to specify the selected X-ray tube is reported to the control apparatus 2 through the communication cable 30. The control apparatus 2 automatically selects the X-ray image output apparatus corresponding to the reported X-ray tube according to the predetermined correspondence. Because the operator may select only the X-ray tube (it-is not necessary to select the X-ray image output apparatus), the increase of efficiency can be attained, and simultaneously, the possibility that the correspondence of the X-ray tube to the X-ray image output apparatus is erroneously selected, is-deleted.

At this time, when the information by which the automatically selected X-ray image output apparatus can be specified, is displayed on the display means 220 of the control apparatus 2, the operator can instantaneously confirm that which X-ray image output apparatus is to be used, before the radiography.

Further, the system may be structured in such a manner that, when one of 3 X-ray image output apparatus 1a, 1b, and 1c is selected by the control apparatus 2, the information specifying the X-ray tube corresponding to the selected X-ray image output apparatus is reported to the X-ray generation control apparatus 3 through the communication cable 30. In this case, the X-ray generation control apparatus 3 automatically selects the X-ray tube instructed from the control apparatus 2.

In this case, because the operator may select only the X-ray image output apparatus (it is not necessary to select the X-ray tube), the increase of efficiency can be attained, and simultaneously, the possibility that the correspondence of the X-ray tube to the X-ray image output apparatus is erroneously selected, is deleted.

At this time, when the information by which the automatically selected X-ray tube can be specified, is displayed on the display means 220 of the control apparatus 2, the operator can instantaneously confirm that which X-ray tube is to be used, before the radiography.

Figure 5:
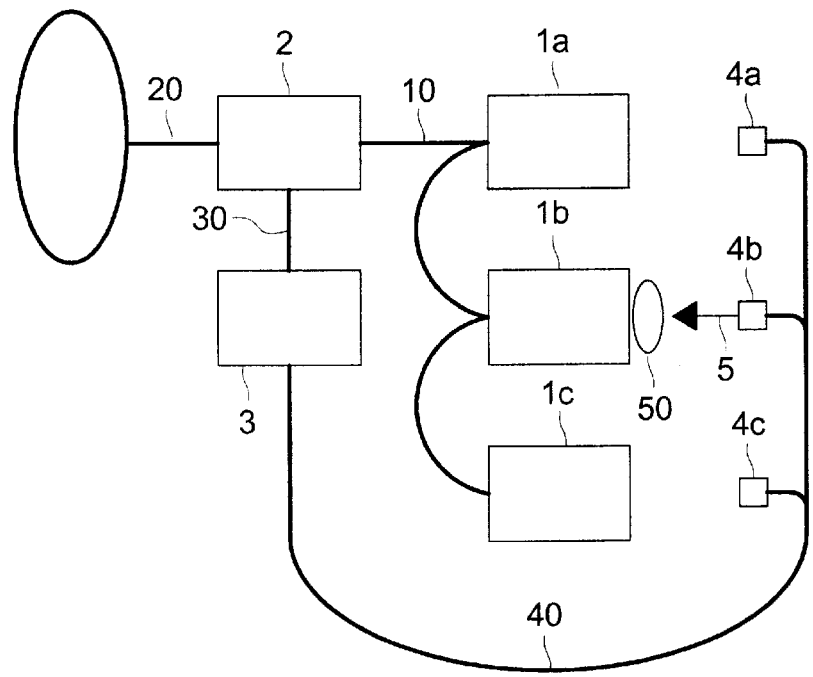
FIG. 5 is a view showing a structural example of an X-ray image radiographing system having a plurality of exclusive use X-ray image output apparatus.

FIG. 5 shows an example when the X-ray radiographing is conducted by using the X-ray tube 4b. The present example is an example of the method by which the operator selects the X-ray tube (the X-ray image output apparatus is automatically selected), however, it is needless to say that it may also be a method by which the operator selects the X-ray image output apparatus (the X-ray tube is automatically selected).

Initially, the operator sets the subject 50, that is, the patient who is subject to radiography, at a position at which the radiographing can be conducted, to the X-ray image output apparatus 1b.

Next, the X-ray tube 4b is selected by the X-ray generation control apparatus 3. When the X-ray tube 4b is selected by the X-ray generation control apparatus 3, the information to specify the selected X-ray tube, for example, the ID number of the X-ray tube 4b is reported to the control apparatus 2 through the communication cable 30.

The operator confirms the patient information inputted through the input means 210, or other image data-attached information through the display means 220. Further, the condition such as the radiographing region or radiographing direction is newly inputted or changed from the conditional input means 221 at need. As the input of the patient information, any one of the case where the information is inputted before the radiographing, and the case where it is inputted after the radiographing, may be adopted.

When each kind of conditions are settled, the operator operates the X-ray generation control apparatus 3 and instructs the generation of the X-ray to the X-ray tube 4b. When the generation of the X-ray is instructed by the operator, the X-ray generation control apparatus 3 makes the already selected X-ray tube 4b generate the X-ray. That is, the X-ray 5 is irradiated from the X-ray tube 4b toward the subject 50. At this time, the timing at which the X-ray is generated, is informed also to the control apparatus 2 through the communication cable 30.

The control apparatus 2 issues the X-ray image read-out instruction to the X-ray image output apparatus 1b almost in timed relationship with the generation timing of the X-ray so that the X-ray image information detected by the detecting means 100 in the X-ray image output apparatus 1b can be read out at once.

Figure 2:
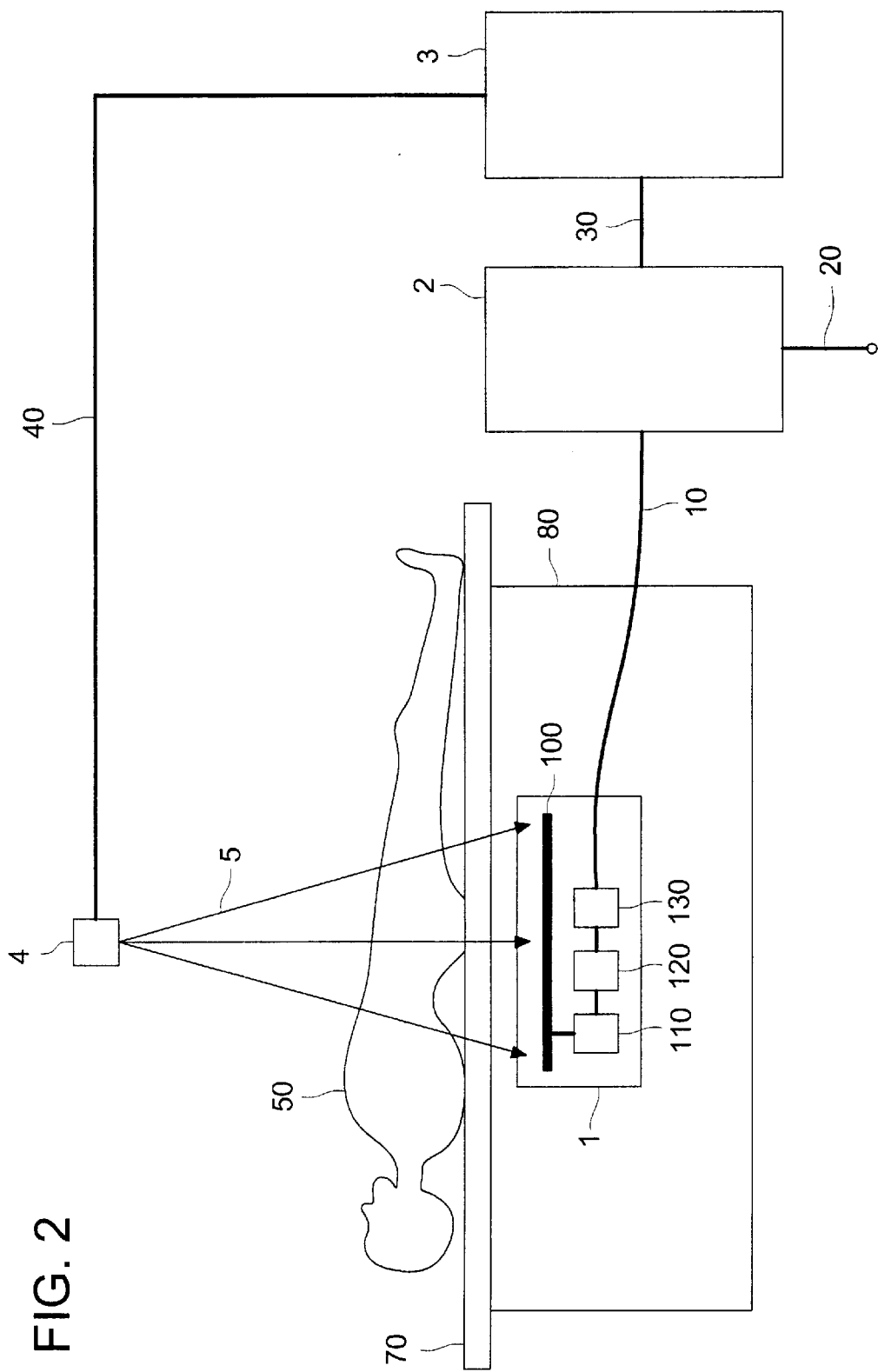
FIG. 2 is a view showing a structural example of a lying type X-ray image radiographing system.

The X-ray image output apparatus 1b which received the X-ray image read-out instruction from the control apparatus 2 converts the X-ray image information detected by the detecting means 100 into the image data according to the main points described in FIG. 1 and FIG. 2.

The generated image. data is transmitted to the control apparatus 2 through the communication means 130, communication cable 10, and communication means 231, and is made to correspond to the image data-attached information and temporarily stored in the storage means 238, and simultaneously, displayed on the display means 220 as an image. The operator confirms whether the normal radiographing can be conducted, by viewing the image of the image data displayed on the display means 220.

The image data temporarily stored in. the storage means 238 is read out by the image processing means 237, and after a predetermined correction processing or image processing is conducted, the image data is made to correspond to the image data-attached information and stored in the storage means 238 again.

The image data after the image processing is displayed again on the display means 220, and it makes the operator enable to confirm whether normal image processing can be conducted. When the information of the X-ray image output apparatus used for the radiography, or the information by which the kind of the X-ray image output apparatus can be specified, is made to correspond to the image data and stored, even when a very long period of time has passed, because the radiographed X-ray image output apparatus can be specified at once, it is very convenient. Specifically, in the case where a person other than the operator refers to the image data, when any disadvantage is discovered in the image data, there is a merit that the image data can be specified soon by which X-ray image output apparatus it is radiographed.

Further, at an appropriate time before or after the X-ray generation, when the X-ray radiographing condition set in the X-ray generation control apparatus 3, that is, the information such as the X-ray irradiation time, the current value flowing through the X-ray tube, and the tube voltage of the X-ray tube, is informed from the X-ray generation control apparatus 3 to the control apparatus 2, and as the image data attached information, it is made to correspond to the image data, and stored in the storage means 238 in the control apparatus 2, because it can be discriminated later under which condition the obtained image is radiographed, which is very convenient.

Further, when the X-ray radiographing condition is displayed on the display means 220, because the operator can confirm again the X-ray radiographing condition, it is more preferable. The image data stored in the storage means 238 of the control apparatus 2 and the image data-attached information are outputted at need onto the communication cable 20 by the communication means 235.

Figure 6:
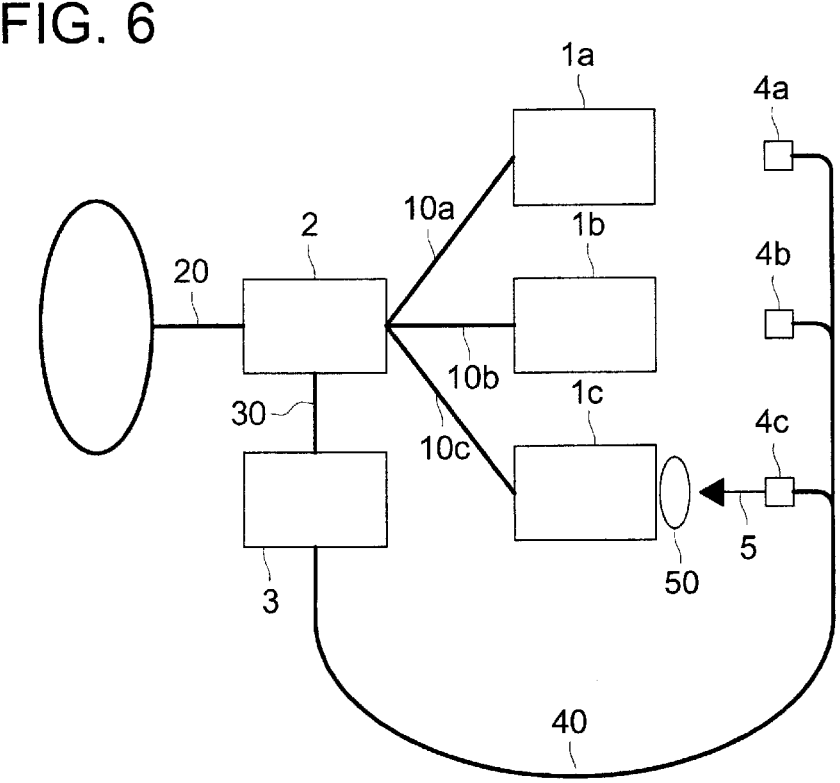
FIG. 6 is a view showing another structural example of an X-ray image radiographing system having a plurality of exclusive use X-ray image output apparatus.

The X-ray image radiographing system in FIG. 6 is an example in which the connection method among the control apparatus 2 and the X-ray image output apparatus 1a, 1b, 1c of the X-ray image radiographing system in FIG. 5, is changed.

In FIG. 5, as the structure, the X-ray image output apparatus 1a, 1b, and 1c are successively connected onto the communication cable 10, however, in FIG. 6, the X-ray image output apparatus 1a, 1b, and 1c are separately connected to the control apparatus 2 by 3 communication cables 10a, 10b and 10c.

In this connection method, because one communication cable is allotted to one X-ray image output apparatus, the communication speed of the control apparatus 2 and X-ray image output apparatus 1a, 1b and 1c becomes high. Further, it is not necessary that the specification of the communication means 130 housed in X-ray image output apparatus 1a, 1b, and 1c, the specification of the communication cable connected to the communication means 130, or kind of the communication protocol, are common among all connected X-ray image output apparatus, the optimum design can be conducted on respective X-ray image output apparatus. As described above, in the present invention, one control apparatus can control a plurality of X-ray image output apparatus having different communication specifications without any problem. For other operations, because these are same as in the X-ray image radiographing system in FIG. 5, the explanation will be omitted.

In the X-ray image radiographing system shown in FIG. 5 and FIG. 6, because one control apparatus 2 can serve irrespectively of the number of connected X-ray image output apparatus 1, when more than 2 connected X-ray image output apparatus 1 are used, the low cost system can be, supplied. Further, because the one control apparatus 2 can serve for more than 2 X-ray image output apparatus 1, when more than 2 X-ray image output apparatus 1 are used, the installation area of the control apparatus 2 can be decreased to the installation area for one apparatus.

Further, in the present invention, because the plurality of X-ray image output apparatus 1 is controlled by one control apparatus 2, when the patient information inputted from the patient information input means 210, or the image processing condition inputted from the conditional input means 221, the image data-attached information such as the kind of radiographing system, radiographing region, and radiographing direction, is inputted only once to the control apparatus 2, because these information can be made to correspond also to the image data read out by any X-ray image output apparatus 1, it is not necessary that these information are inputted for each X-ray image output apparatus.

Further, in the present invention, because the using X-ray tube 4 and the X-ray image output apparatus 1 controlled by the control apparatus 2 are made to correspond to each other and controlled, the possibility the operator mistakes the correspondence of the X-ray image output apparatus 1 to the X-ray tube 4, is removed. Further, the time to select both of the X-ray image output apparatus 1 and the X-ray tube 4 is deleted, and the system is structured such that the radiographing can be conducted by only selecting any one of them.

Next, by using FIG. 7, another embodiment of the X-ray image radiographing system which is the present invention, that is, an embodiment of a cassette correspondent type the X-ray image radiographing system will be described. In the present example, 3 X-ray image output apparatus 1d, 1e, and 1f are successively connected onto the communication cable 10. Because the effect of the successive connection is the same as the content described in FIG. 5, the explanation will be omitted here.

The X-ray image output apparatus 1d, 1e, and 1f are controlled by one control apparatus 2 through the communication cable 10. The control apparatus 2 controls 3 X-ray image output apparatus 1d, 1e, and 1f by, for example, ID number.

The present example is an example in which the one control apparatus 2 controls 3 X-ray image output apparatus 1d, 1e, and 1f, however, the present invention does not limit the number of X-ray image output apparatus to be controlled by the control apparatus 2.

Further, in the present example, a cassette correspondent X-ray image radiographing system using the stimulative fluorescent substance will be described, however, it is of course that a cassette correspondent X-ray image radiographing system using the solid state plane detector can also structure the connection between the X-ray image output apparatus and the control apparatus in the same manner.

Initially, the operator sets the subject 50 and the cassette 6 at an optimum position in the X-ray irradiation area of the X-ray tube.

The operator confirms the patient information inputted through the patient information input means 210, or other image data-attached information through the display means 220. Further, the operator newly inputs the conditions such as the radiographing region and radiographing direction from the conditional inputting means 221, or changes them, at need. The input of the patient information may adopts any of the case where it is inputted before the radiographing, or the case where it is inputted after the radiographing.

When each condition is settled, the operator operates the X-ray generation control apparatus 3, and instructs the generation of the X-ray to the X-ray tube 4. When the generation of the X-ray is instructed by the operator, the X-ray generation control apparatus 3 generates the X-ray from the X-ray tube 4 through the cable 40. That is, the X-ray 5 is irradiated from the X-ray tube 4 to the subject 50.

When the irradiation of the X-ray is completed, the operator inserts the cassette 6 into any one of the X-ray image output apparatus 1d, 1e, and 1f. In the present invention, the number of the cassette insertion ports of the X-ray image output apparatus is not limited.

The operator can continuously conduct a plurality of times of radiographing on the subject 50 by using a plurality of sheets of cassettes. In this case, a plurality of sheets of cassettes to which the radiographing is completed, may be simultaneously inserted into respective of(or a part of) X-ray image output apparatus 1d, 1e, and 1f.

Figure 3:
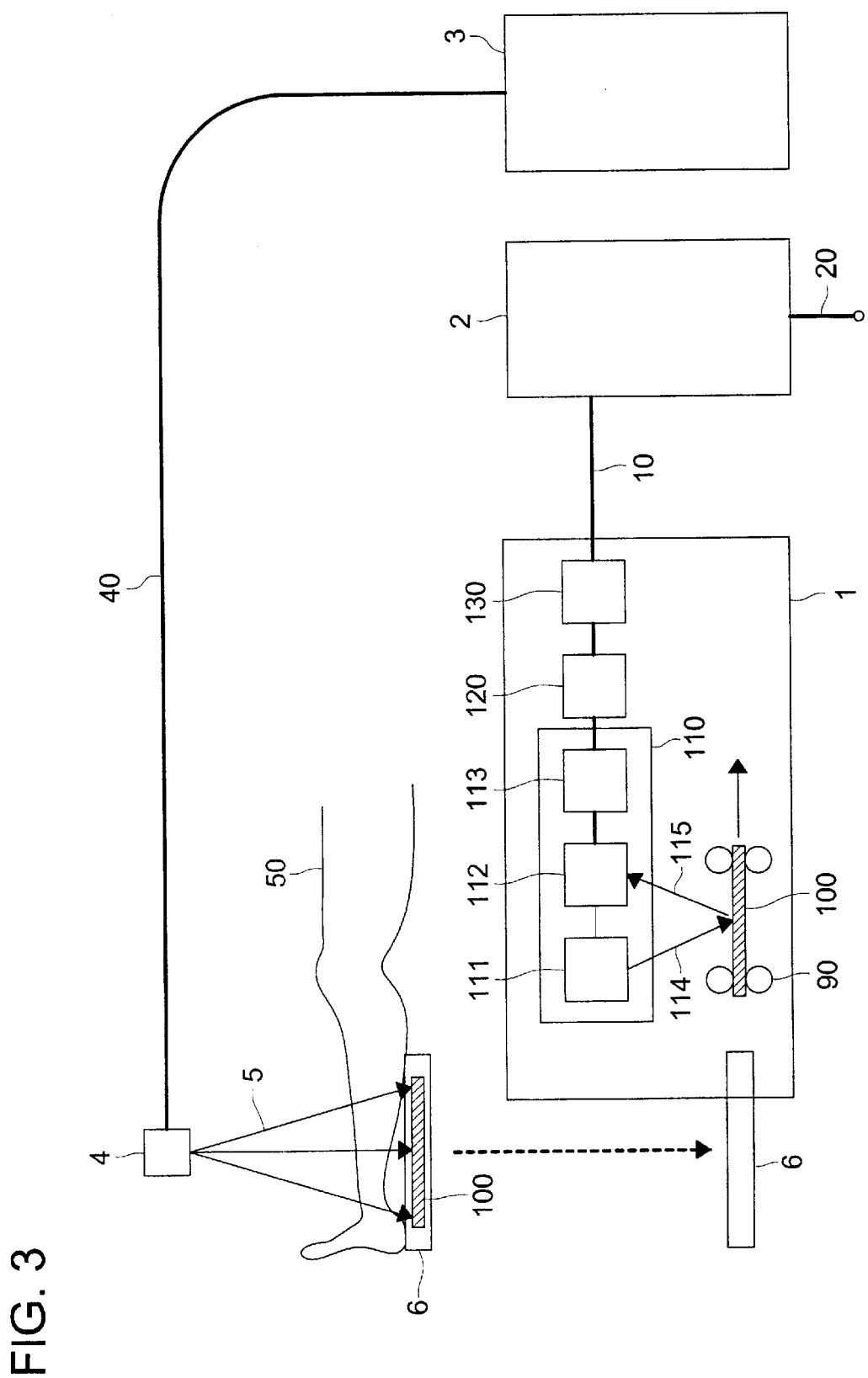
FIG. 3 is a view showing a structural example of a cassette correspondent type X-ray image radiographing system.

When the cassette is inserted into any one of X-ray image output apparatus 1d, 1e, and 1f, the insertion of the cassette makes a trigger, and the stimulative fluorescent substance plate which is the detecting means 100, is pulled out, and the image data is generated according to the main points described in FIG. 3. Which of X-ray image output apparatus 1d, 1e, and 1f the control apparatus 2 is to control, is determined by referring to the information whether the cassette is inserted into the X-ray image output apparatus.

The generated image data is transmitted to the control apparatus 2 through the communication 130, communication cable 10, and communication 231, and these are made to correspond to the image data-attached information and temporarily stored in the storage means 238, and simultaneously displayed on the display means 220 as an image. The operator confirms whether the normal radiographing can be conducted, by viewing the image displayed on the display means 220. The image data temporarily stored in the storage means 238 is read out by the image processing means 237, and after a predetermined correction processing or image processing is conducted, it is made to correspond to the image data-attached information and stored again in the storage means 238. The system is structured such that the image data after the image processing is displayed again on the display means 220, and the operator can confirm whether the normal image processing can be conducted.

Figure 7:
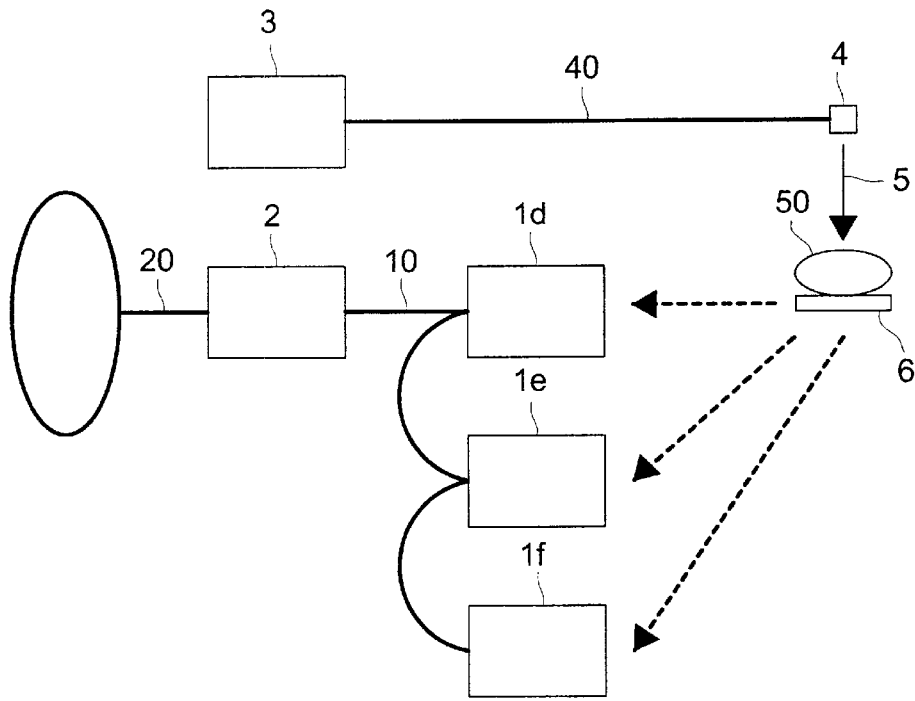
FIG. 7 is a view showing a structural example of an X-ray image radiographing system having a plurality of cassette correspondent type X-ray image output apparatus.

Further, although not shown in FIG. 7, in the same manner as in FIG. 5 and FIG. 6, the communication cable 30 may be provided between the control apparatus 2 and the X-ray generation control apparatus 3 so that the control apparatus 2 and the X-ray generation control apparatus 3 can communicate with each other. In this case, the control means can obtain from the X-ray generation control apparatus 3 the X-ray radiographing condition such as the X-ray irradiation time, the current value flowing through the X-ray tube, and the tube voltage of the X-ray tube, and the obtained X-ray radiographing condition can be made to correspond to the image data as a part of the image data-attached information, and stored in the storage means 238 in the control apparatus 2.

The image data and the image data-attached information stored in the storage means 238 in the control apparatus 2 are outputted onto the communication cable 20 at need by the communication means 235.

In the present invention, the control apparatus 2 may be an apparatus having a separate casing from the X-ray image output apparatus 1, or it may be housed in any one apparatus of X-ray image output apparatus 1d, 1e, and 1f.

Figure 8:
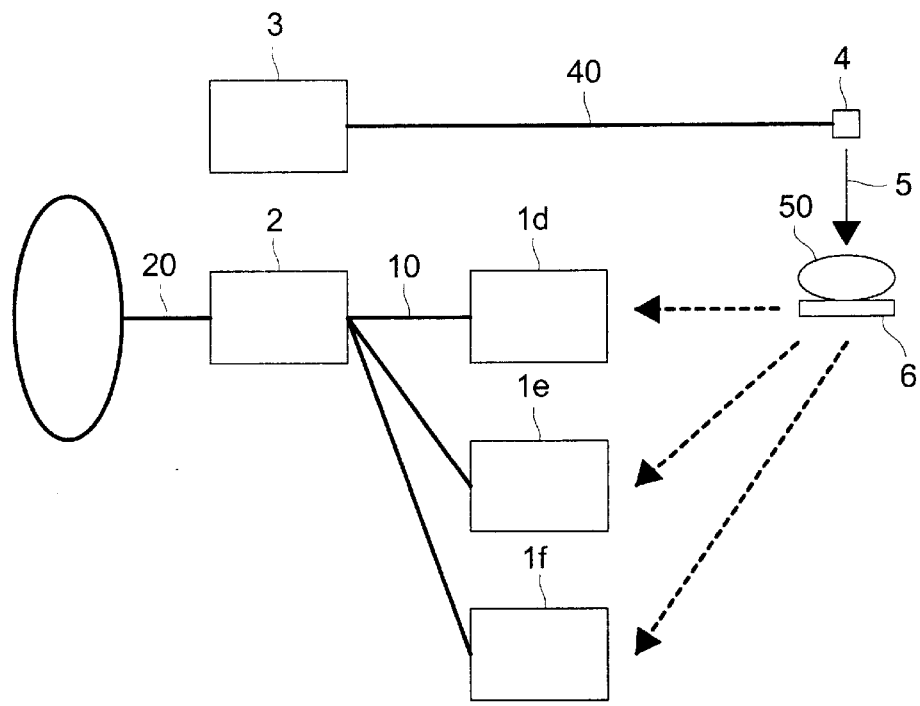
FIG. 8 is a view showing another structural example of an X-ray image radiographing system having a plurality of cassette correspondent type X-ray image output apparatus.

The X-ray image radiographing system in FIG. 8 is an example in which the connection method among the control apparatus 2 and X-ray image output apparatus 1d, 1e, and 1f of the X-ray image radiographing system in FIG. 7 is changed.

In FIG. 7, the X-ray image output apparatus 1d, 1e, and 1f are structured such that these are connected in serial onto the communication cable 10, however, in FIG. 8, X-ray image output apparatus 1d, 1e, and 1f are connected to the control apparatus 2 separately by 3 communication cables 10d, 10e, and 10f.

Because the X-ray image radiographing system having such the connection method has the same effect as the X-ray image radiographing system described in FIG. 6, the explanation herein will be omitted.

Because other operations are the same as in the X-ray image radiographing system, the explanation will be omitted.

In the X-ray image output apparatus 1 of the X-ray image radiographing system described in FIG. 7 or FIG. 8, the number of the X-ray image output apparatus 1 connected to the control apparatus 2 can be changed corresponding to a scale of the facilities or the radiographing frequency of the X-ray.

For example, in the facilities in which the radiographing frequency is samll, or the facilities in which many radiographing are not conducted on one patient at one time, it is sufficient that one X-ray image output apparatus 1 is connected to one control apparatus 2.

In the facilities in which the radiographing frequency is large, or the hospital in which many radiographing are conducted on one patient at one time, when a plurality of X-ray image output apparatus 1 are connected to one control apparatus 2, the processing capacity of the X-ray image radiographing system can be increased.

As described above, in the X-ray image radiographing system of the present invention, because one control apparatus 2 is sufficient irrespective of the number of the connected X-ray image output apparatus 1, when the number of the connected X-ray image output apparatus 1 is more than 2, the low cost system can be provided.

Further, when the control apparatus 2 is structured by a separated casing from the X-ray image output apparatus 1, one control apparatus 2 is sufficient for more than 2 X-ray image output apparatus 1, when more than 2 X-ray image output apparatus 1 are used, the installation area of the control apparatus 2 can be served by that of one set.

Further, when m X-ray image output apparatus 1 having the cassette insertion port with slots for n sheets are connected, because maximum n×m sheets of cassettes can be continuously inserted, when it is desired to process large number of cassettes at a time, there is no trouble of taking-out and inserting-in of the cassette, and the radiographing cycle time can be reduced.

Further, when m X-ray image output apparatus 1 are connected to the control apparatus 2, because m X-ray image output apparatus 1 can read out the image data simultaneously, the read-out time when a large number of cassettes are simultaneously read out, is reduced to 1/m. In this case, when it is compared to one X-ray image output apparatus 1 having the cassette insertion port with n×m slots per one apparatus, these apparatus can be regarded as an apparatus whose throughput is m times. Further, because the plurality of X-ray image output apparatus 1 are controlled by one control apparatus 2, when the patient information inputted from the patient information input means 210, image processing condition inputted from the conditional input means 221, and the image data-attached information such as the kind of radiographing apparatus, radiographing region, and radiographing direction, are inputted to the control apparatus 2 only once, because these information can be made to correspond to also the image data read out by any X-ray image output apparatus, it is not necessary that these information are inputted for each of X-ray image output apparatus.

Figure 9:
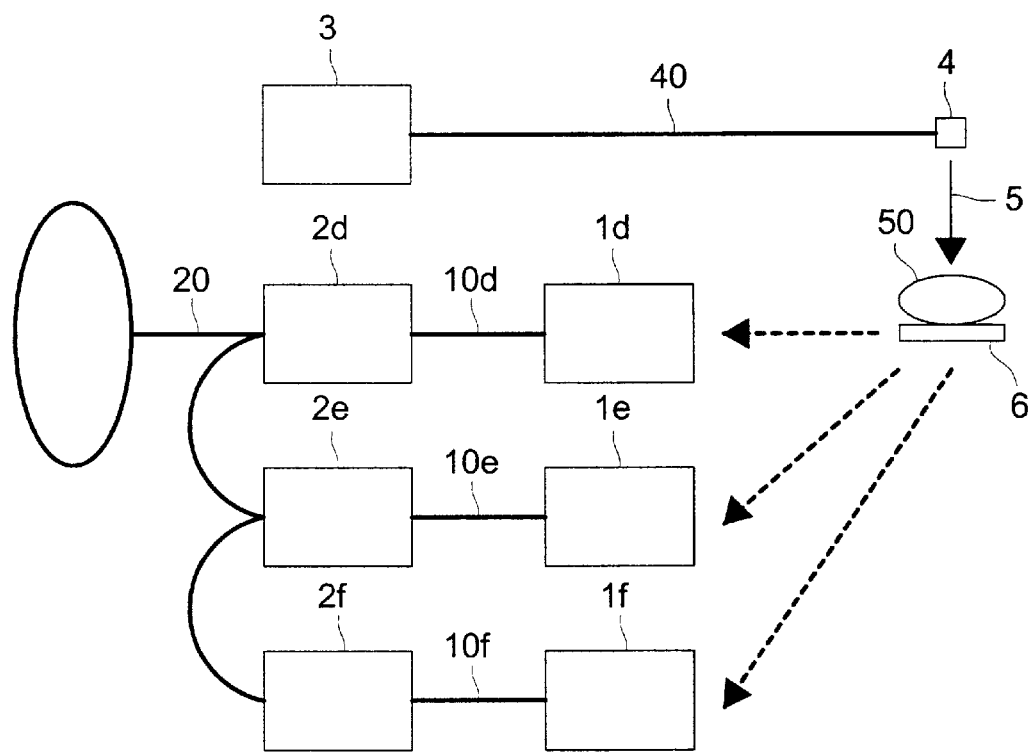
FIG. 9 is a view showing a still another structural example of an X-ray image radiographing system having a plurality of cassette correspondent type X-ray image output apparatus.

The X-ray image radiographing system in FIG. 9 is a modified example of the X-ray image radiographing system shown in FIG. 7 and FIG. 8. In FIG. 7 and FIG. 8, a plurality of X-ray image output apparatus 1d, 1e, and 1f are controlled by one control apparatus 2, however, in FIG. 9, control apparatus 2d, 2e, and 2f are connected to a plurality of X-ray image output apparatus 1d, 1e, and 1f by 1 to 1, through communication cables 10d, 10e, and 10f. The control apparatus 2d, 2e, and 2f are structured such that these can communicate with each other by the communication cable 11, and the patient information, image processing condition, the image data-attached information such as the radiographing region, and radiographing direction can be held in common among respective control apparatus 2d, 2e, and 2f.

Each of control apparatus 2d, 2e, and 2f may have the patient information input means 210. In this case, there is a merit that the operator can input the patient information from any control apparatus.

Further, the system may be structured such that any one of control apparatus 2d, 2e, and 2f has the patient information input means 210. In this case, the operator can not input the patient information only from the control apparatus to which the patient information input means 210 is connected, however, there is a merit that the cost of the X-ray image radiographing system can be decreased.

Further, each of control apparatus 2d, 2e, and 2f may have the display means 220. In this case, there is a merit that the operator can confirm the image data or the image data-attached information from any one of control apparatus, and the operation efficiency can be increased. Specifically, when a plurality of cassettes are read out by a plurality of X-ray image output apparatus at almost same time, because the image can be displayed by a plurality of display means, there is a merit that the speed of the confirming operation of the image data can be increased. Further, the system may be structured such that any one of control apparatus 2d, 2e, and 2f has the display means 220. In this case, the operator can not confirm the image data-attached information or the image data only from the control apparatus to which the display means 220 is connected, however, there is a merit that the cost of the X-ray image radiographing system can be decreased.

In the same manner, the conditional input means 221 may be installed in each of control apparatus 2d, 2e, and 2f, or in any one of control apparatus 2d, 2e, and 2f.

In the X-ray image radiographing system in FIG. 9, when a plurality of cassettes are processed at the same time, because the read-out operation and image processing operation are operated by a plurality of X-ray image output apparatus and control apparatus in parallel, there is a merit that the processing speed of the X-ray image radiographing system is greatly increased. Further, because the image data and the image data-attached information such as the patient information are held in common among respective control apparatus, these can be operated as if these are one apparatus, and there is a merit that, even when these are operated in parallel, the operability is not lowered.

The example and effect of the X-ray image radiographing system in which a plurality of X-ray image output apparatus are connected to a plurality of control means by one to one, is described by using FIG. 9, however, it is clear that the same system can be structured for the exclusive-use type system described in FIG. 5 and FIG. 6. In that case, the same effect as described in FIG. 9 can be obtained.

Figure 10:
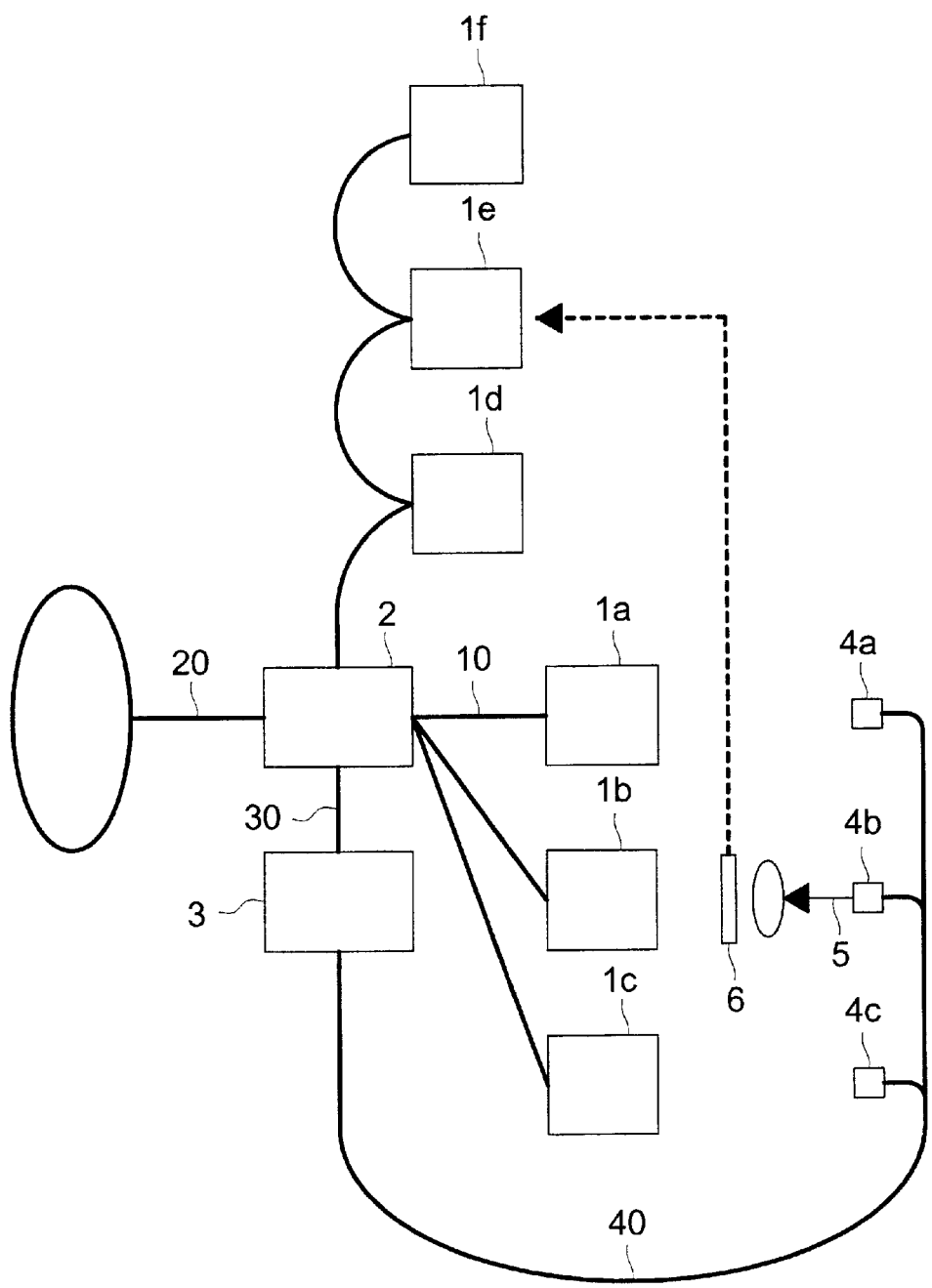
FIG. 10 is a view showing a structural example of an X-ray image radiographing system having a plurality of exclusive use type X-ray image output apparatus and cassette correspondent type X-ray image output apparatus.

The X-ray image radiographing system in FIG. 10 is an example of a composite system of the exclusive-use type X-ray image radiographing system shown in FIG. 5, FIG. 6, and FIG. 9, and the cassette correspondent type X-ray image radiographing system shown in FIG. 7, FIG. 8, and FIG. 9.

The present example is an example structured such that the exclusive-use type X-ray image radiographing system in FIG. 6 and the cassette correspondent type X-ray image radiographing system in FIG. 7 are made in common, and are controlled by one control apparatus, however, the present invention is not limited to only the combination of the present example. For example, the system may be a combination of the exclusive-use type X-ray image radiographing system in FIG. 5 and the cassette correspondent type X-ray image radiographing system in FIG. 8, or the other combination.

The present example has the effects in which the effects described in respective X-ray image radiographing systems are added, and can structure the most effective system.

Because the operations of the present example is according to the operations of the exclusive-use type X-ray image radiographing system in FIG. 6 and the cassette correspondent type X-ray image radiographing system in FIG. 7, the explanation will be omitted.

Figure 11:
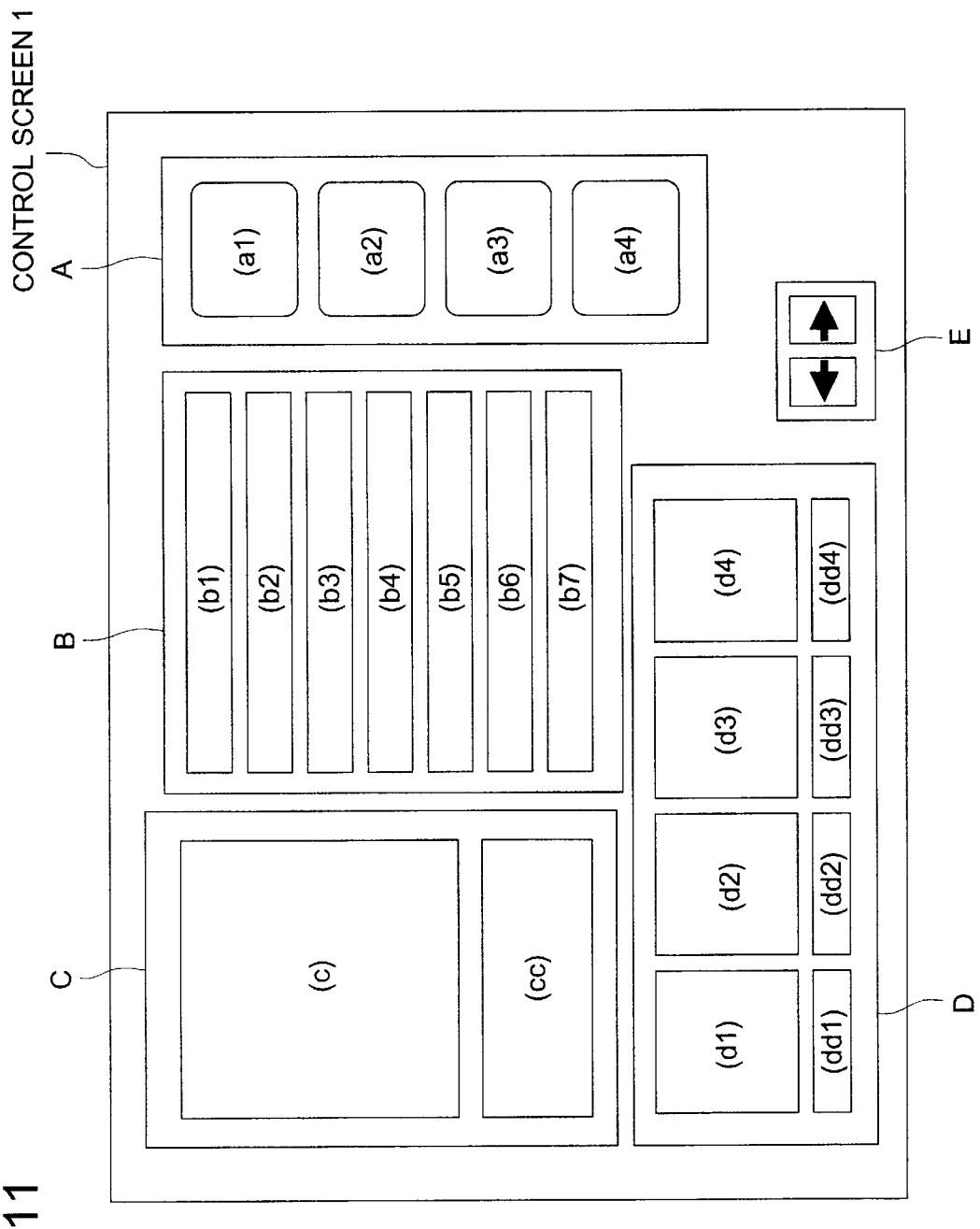
FIG. 11 is a view showing an example of a control image plane.

Next, by using FIG. 11 and FIG. 12, another embodiment of the X-ray image radiographing system which is the present invention, will be described. FIG. 11 is an example of a control image plane 1 displayed on the display means 220 of the control apparatus 2. Because a touch panel which is the conditional input means 221 is equipped on the display means 220, when the displayed image plane is touched, the conditions can be inputted, instructed, or selected.

Incidentally, in the present example, the explanation will be conducted by using an example in which the touch panel is used as the conditional input means 221, however, in the present example, the conditional input means 221 is not limited to the touch panel. Other means, for example, the keyboard, mouse, trackball, or voice input apparatus may be used.

An image plane A (a selecting section) is an image pale by which the X-ray image output apparatus 1 connected to the control apparatus 2 is selected, or selected X-ray image output apparatus 1 is displayed. On icons (a1)–(a4), the names or rough sketches of a plurality of X-ray image output apparatus 1 connected to the control apparatus 2 are displayed, and when any one of icons is touched, the X-ray image output apparatus 1 to be used can be selected.

Further, when the X-ray image output apparatus 1 is designated by the X-ray generation control apparatus 3, that is, when the operator designates the X-ray tube 4 to be used by the X-ray generation control apparatus 3, and the control apparatus 2 automatically selects one from a plurality of the X-ray image output apparatus 1 according to the designated X-ray tube 4, an icon corresponding to the automatically selected X-ray image output apparatus 1 flickers, its density is reversed, or its color is changed, thereby, which is the automatically selected X-ray image output apparatus 1, is noticed to the operator.

Because, on (b1)–(b7) of the image plane B, the reserve information of the radiography, for example, the ID information, or name of the patient, radiographing region, or radiographing direction, is displayed, the operator can not only confirm a turn of the patient to be radiographed, but also can know previously which radiographing is to be conducted after now.

A (c) of the image plane C is an image plane displaying an image of the image data read out by the X-ray image output apparatus 1. When the image data outputted by the X-ray image output apparatus 1 is received by the control apparatus 2, an image of the received image data is displayed on the image plane (c).

Further, when the image processing is conducted on the received image data by the image processing means 237, the image displayed on the image plane (c) is changed from the image of the image data before the image processing to the image of the image data after the image processing.

Further, the previously radiographed image data is read out, and can also be displayed on the image plane (c).

On a (cc) of the image plane C, a part of the image data-attached information of the image data displayed on the image plane (c) is displayed. For example, the patient name, the ID number of the patient, the radiographing region, and radiographing direction, are displayed. Therefore, the operator can confirm again the attached information of the image data displayed on the image plane (c).

On a (d1)–(d4) of the image plane D, an image of the reduction image of the previously radiographed image data is displayed. Further, on image planes (dd1)–(dd4), a part of the image data-attached information corresponding to each of the reduction images (d1)–(d4), for example, the patient name or the ID number of the patient is displayed.

The image of the reduction image and the image data-attached information displayed on the image planes (d1)–(d4) and image planes (dd1)–(dd4) are arranged from the image plane (d1) to the image plane (d4) in the order of the image from the newest time to the older time. Herein, the "time" may be any one of the time at which the X-ray radiographing system receives the reserve registration of the radiographing or its equivalent time, the time at which the X-ray is irradiated onto the subject 50 or its equivalent time, the time at which the image data is generated in the X-ray image output apparatus 1 or its equivalent time, or the time at which the control apparatus 2 receives the image data or its equivalent.

Because the operator can refer to and confirm the visualized past radiography according to the order in time series such as radiographing time, the efficiency of the referring and confirming operation can be greatly increased.

When the control apparatus 2 receives the new image data, and the image of the received new image data is displayed on the image plane (c), the image of the image data displayed till now on the image plane (c) is reduced and newly displayed at a position of (d1). At this time, the reduction images displayed on the (d1)–(d3) till that time respectively moved in the direction of the (d4) by each 1, and displayed on (d2)–(d4), and the reduction image displayed on the (d4) till that time is not displayed on the image plane.

The timing at which the image of the received new image data is reduced and newly displayed on the image plane (c) may be the timing at which the radiographing of the image plane (c) is approved. That is, this system is structured such that the control image plane 1, an OK-button which approves the image of the image data displayed on the image plane (c), and a re-radiography-button which requires the re-radiographing (photographs again) are displayed, and when the OK-button is selected, the image of the new image data received on the image plane (c) is reduced, and newly displayed at the position of (d1). When there-radiography-button is selected, the image of the image data displayed on the image plane (c) is erased, and this system is ready for the next re-radiographing.

The images displayed on the image planes (d1)–(d4), may be limited to only the image of the same patient (subject) as the image of the image data displayed on the image plane (c). That is, when a plurality of X-ray image are radiographed for the same patient, the image data which is received at last by the control apparatus 2, is displayed on the image plane (c), and the image data received by the control apparatus 2 before that time, is displayed on the image planes (d1)–(d4). Next, when the radiography of the different patient is conducted, the images of the image data displayed on the image planes (d1)–(d4) are deleted from the image planes. It is of course that, in company with this operation, the image plane (cc) and the image planes (dd1)–(dd4) are also operated in the similar relationship.

When the icon of the arrow facing the right direction or the left direction shown on the image plane E is touched, the image of the reduction image displayed on (d1)–(d4) of the image plane D and the image data-attached information displayed on the image planes (dd1)–(dd4) are scrolled in the arrowed direction and displayed again. That is, because this system is structured such that, by the operation of the image plane E, the image of the radiographed reduction image and the image data-attached information are successively scrolled and displayed on the image planes (d1)–(d4) and (dd1)–(dd4) according to the order of the time series, the image can be referred to and confirmed, going back to the past arbitrary time.

Further, the system is structured such that, when any one of the images of the reduction images is touched, the touched image of the reduction images is enlarged, and displayed on the image plane (c). In this case, on the image plane (cc), the image data-attached information corresponding to the newly displayed image data image is displayed.

Further, it may also be structured such that, when any one of the images of the reduction images is touched, the touched image of the reduction images is enlarged, and displayed on the image plane other than the newly generated image plane (c).

Figure 12:
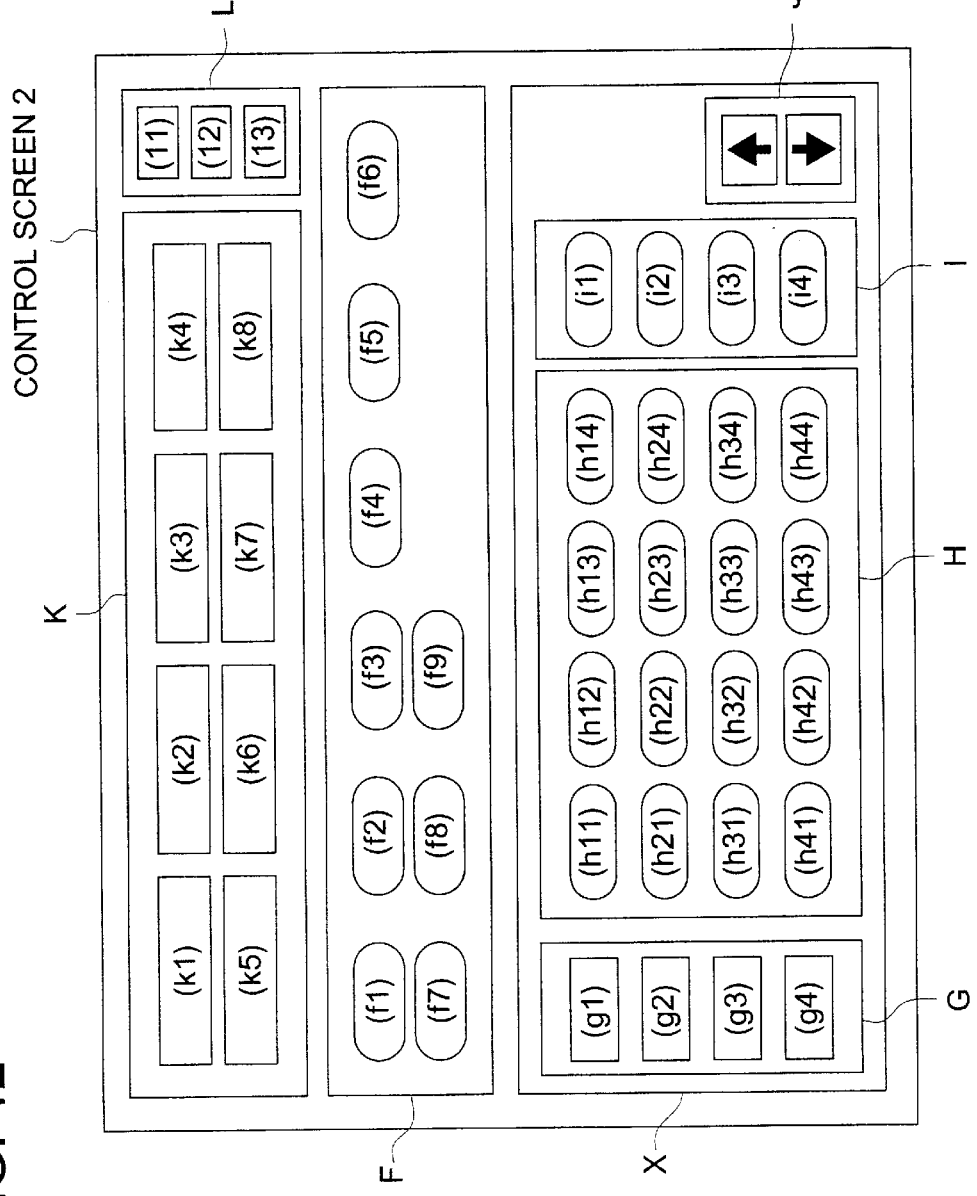
FIG. 12 is a view showing an example of another control image plane.

FIG. 12 is an example of the control image plane 2 displayed on the display means 220 of the control apparatus 2.

Large classifications of the radiographing regions are displayed on icons (f1)–(f9) on the image plane F. The large classifications are rough classifications according to the main components of the human body such as, for example, the head, the chest, the abdomen, the arms, the legs, the backbone, and the basin. When the operator selects the part to be radiographed from the icons (f1)–(f9), and touches it, the large classification of the part desired to be radiographed is informed to the control apparatus 2.

In the present invention, corresponding to the X-ray image radiographing apparatus registered on the image plane A, the name of the part of the large classification displayed on the image plane F is controlled.

For example, when the stand alone type, lying type, and cassette correspondent type of 3 X-ray image radiographing apparatus are registered on the image plane A, that is, when the stand alone type, lying type, and cassette correspondent type of 3 X-ray image radiographing apparatus are registered in the control apparatus 2, in the large classification on the image plane F corresponding to the stand alone type, for example, 5 items of the chest, the abdomen, a lumber, the arms, and the legs are registered. Further, in the large classification on the image plane F corresponding to the lying type, for example, 8 items of the head, the chest, the abdomen, the backbone, the basin, the arms, the legs, and soft parts and others are registered. Further, in the large classification on the image plane F corresponding to the cassette correspondent type, for example, 9 items of the head, the chest, the abdomen, the backbone, the basin, the arms, the legs, soft parts and others, and a newborn are registered.

When the operator selects the icon of the stand alone type on the image plane A, on the image plane F, the 5 items of the chest, the abdomen, a lumber, the arms, and the legs, when the operator selects the icon of the lying type on the image plane A, on the image plane F, the 8 items of the head, the chest, the abdomen, the backbone, the basin, the arms, the legs, and soft parts and others, and when the operator selects the icon of the cassette correspondent type on the image plane A, on the image plane F, 9 items of the head, the chest, the abdomen, the backbone, the basin, the arms, the legs, soft parts and others, and a newborn, are displayed in any one of (f1)–(fg) of the image plane F as the choices.

As described above, in the present invention, because the system is controlled such that, to the selected X-ray image radiographing apparatus, the previously registered large classifications are displayed, and excess large classifications (large classifications which are not used in the selected X-ray image radiographing apparatus) are not displayed, when the operator selects the large classification, the operator is not confused, and can select the target large classification in a short time.

When the X-ray image radiographing apparatus and the large classification are decided, on (g1)–(g4) of the image plane G, a small classification of the radiographing regions corresponding to the decided X-ray image radiographing apparatus and large classification is displayed as the choices. The small classification of the radiographing regions is the classification in which the regions shown by the large classifications are classified to further small regions, and for example, when the large classification is the arm, the shoulder joint, a shoulder blade, acromioclavicular joint, a humerus, the elbow joint, the forearm bone, a hand joint, carpals, a finger bone, are small classification. On (h11)–(h14) of the image plane H, the radiographing direction corresponding to the small classification (g1), on (h21)–(h24), the radiographing direction corresponding to the small classification (g2), on (h31)–(h34), the radiographing direction corresponding to the small classification (g3), and on (h41)–(h44), the radiographing direction corresponding to the small classification (g4), are displayed as the choices.

When representative radiographing directions will be introduced here, there are PA: Posteroanterior Projection, AP: Anteroposterrior Projection, LAT: Lateral Radiography, and Oblique Radiography.

In the present invention, the small classification and the radiographing direction are registered for each of combination of the X-ray image radiographing apparatus and the large classification. Because the system is controlled such that, for the combination of the X-ray image radiographing apparatus and the large classification, the previously registered small classification and the radiographing direction are displayed as the choices, and excess small classifications and the radiographing directions (small classification and the radiographing direction not used in the combination of the selected X-ray image radiographing apparatus and the large classification) are not displayed, when the operator selects the small classification and the radiographing direction, the target small classification and radiographing direction can be selected in a short time, without being confused.

On (i1)–(i4) of the image plane I, set radiography menus corresponding to the small classifications (g1)–(g4) are displayed as the choices. The set radiography is a set of frequently used several radiographing directions, and there is a set of 2 direction radiography or a set of 3 direction radiography. For example, when a set radiography menu in which the radiography of 3 directions of Posteroanterior Projection, Anteroposterrior Projection, and Lateral Radiography is registered, is selected, the 3 radiographing directions of Posteroanterior Projection, Anteroposterrior Projection, and Lateral Radiography are selected at a time. Accordingly, a time in which the operator selects the 3 radiographing directions individually, can be saved.

It is preferable that the content, the existence or not of the display, or the display order of the large classification, small classification, radiographing direction, or set radiography can be customized corresponding to the fondness of the hospital using this system, or the operator. For example, in some radiographing room, in the case where the large classification, small classification, radiographing direction, and set radiography menu which are not used, exist, when the system can be made so that these are not displayed, it is more convenient.

When the icons with arrows in the upper direction and lower direction are touched, the image plane G, image plane h, and image plane I are synchronized, and scrolled in the arrowed direction. When there are many small classifications and these can not be displayed on the display image plane, the image plane is scrolled by using this icon, and the small classification not displayed on the image plane can be found.

The selected small classification and radiographing direction are successively displayed on (k1)–(k8) of the image plane K. For example, when (1) the large classification=the chest, the small classification=the upper part of ribs, the radiographing direction=PA: Posteroanterior Projection, (2) the large classification=the backbone, the small classification=the thoracic vertebrae, the radiographing direction=AP: Anteroposterrior Projection, and (3) the large classification=the arm, the small classification=a humerus, the radiographing direction=LA: Lateral radiography are registered in this order, the upper part of ribs PA is displayed on the (k1) image pane, the thoracic vertebrae AP is displayed on the (k2) image plane, and the upper arm bone LAT is displayed on the (k3) image plane. When the small classification is displayed, because, even when the large classification dare not be displayed, it can be clear, in the present invention, only the small classification and the radiographing direction are displayed, however, it is no problem that the other information is displayed.

As described above, in the present invention, because the information of the selected radiographing region or radiographing direction is successively displayed on the image plane K, the operator can conduct the operation while always confirming what is selected, and the operation mistake of the operator can be prevented. In the above example, only the information of the radiographing region or radiographing direction is displayed on the image plane K, however, it may also be allowable that the other information, for example, the kind of the X-ray image output apparatus is displayed together with the above information.

An icon (11) of the image plane L is the icon to designates the decision of the information displayed on the image plane K. When this icon is touched, the information of the small classification and the radiographing direction displayed on the image plane K is registered in the storage means 237 in the control apparatus 2, being made to correspond to the patient information, as the decided information.

An icon (12) of the image plane L is the icon to instruct the cancellation of the information displayed on the image plane K. When this icon is touched, the information such as the small classification and radiographing direction displayed on the image plane K. is deleted from the image plane.

An icon (13) of the image plane L is the icon to instruct the deletion of a part of the information displayed on the image plane K. When the icon (13) is touched after the icons (k1)–(k8) which are desired to be deleted, are designated (touched), the information such as the small classification and radiographing direction corresponding to the designated icon, is deleted from the image plane.

Further, the icon (13) of the image plane L may be the icon to instruct the correction of a part of the information displayed on the image plane K. After any icon of (k1)–(k8) which is desired to be corrected is touched, when the icon (13) is touched, the information such as the large classification or the small classification, and the radiographing direction corresponding to the designated icon can be corrected. Herein, when the information such as the large classification or the small classification, and the radiographing direction is newly selected again, the newly selected information is newly displayed on the designated icon portion.

As describe above, in the present invention, because the system is structured such that, for the large classification or the small classification of the selected radiographing region, and the radiographing direction, the decision, cancellation, deletion of a part, or correction of a part can be conducted, even when the operator mistakes the selection, the mistake can be corrected in the shortest time by the minimum operation.

In the present invention, because the image processing means 237 conducts the optimum image processing on the image data according to thus determined radiographing region or the radiographing direction, even when the radiographing region or the radiographing direction is changed, the optimum image finish can be always maintained. Specifically, in the gradation conversion processing, because it is preferable that the parameter of the processing, the kind of processing, and the degree of the processing are optimized, as in the present invention, when the parameter of the processing, the kind of processing, and the degree of the processing are determined corresponding to the difference of the radiographing region or radiographing direction, the optimum image finish can be always maintained. In the present example, only the usable large classification or small classification, and radiographing direction are displayed as the control image plane, however, for example, it may also be allowable that all the large classification or small classification, and radiographing direction are previously displayed, and by changing the color of the display of unusable large classification or small classification, and radiographing direction, the selectable items are informed to the operator. In this case, it is preferable that, even when unusable item is selected, the error information is displayed, and the large classification which is going to be selected, is not received.

As described above, because the X-ray image radiographing system which allows the different detecting means or different type apparatus, and unitedly controls a plurality of X-ray image output apparatus or a plurality of X-ray tubes, can be structured, the circumstances with good operation efficiency in which a time of operations is suppressed to minimum, can be provided.

Further, because, without being limited by the type of the detecting means or apparatus, the X-ray image radiographing system which can control a plurality of X-ray image output apparatus by one control apparatus can be structured, the installation area can be suppressed to minimum, and the system can be easily structured and expanded at low cost, corresponding to the scale of the hospital or the frequency of the radiographing.

Further, because the X-ray image radiographing system by which the selection of the radiographing region or radiographing direction, or the troublesome operation relating to reference to the past images is solved, and the operation mistake of the operator can be prevented and restored, can be structured, the system with good efficiency and high reliability can be provided.

Further, because the image processing means which can automatically cope with the difference of detecting means or the content of correction, is mounted in the X-ray image radiographing system, even when the different detecting means or different type apparatus are connected, the image with the always constant finish and excellent image quality can be provided.

What is claimed is:

1. A X-ray image radiographing system for medical diagnosis, comprising:
   a plurality of X-ray image output apparatus each of which detects X-rays having passed through an object and outputs image data of a medical image of the object on a recording sheet on which the medical image of the object is reproduced for medical diagnosis;
   a control apparatus to control the plurality of the X-ray image output apparatus;
   an object information input device used in common for the plurality of X-ray image output apparatus so as to input plural different sets of object information regarding plural different objects radiographed by the plurality of X-ray image output apparatus; and a storage device used in common for the plurality of X-ray image output apparatus so as to store the image data outputted from the plurality of X-ray image output apparatus and the plural different sets of object information inputted from the object information input device, wherein image data of an object is stored so as to be correlated with a set of object information corresponding to the same object.

2. The X-ray image radiographing system of claim 1, wherein the control apparatus is a common control device to operate and control the plurality of the X-ray image output apparatus.

3. The X-ray image radiographing system of claim 1, wherein the object information is patient information.

4. The X-ray image radiographing system of claim 3, wherein the patient information is name or an ID code of a patient.

5. The X-ray image radiographing system of claim 1, wherein the object information is information regarding a part of a body to be radiographed.

6. The X-ray image radiographing system of claim 1, wherein the control apparatus comprises a plurality of control devices each of which is independently provided to one of the plurality of X-ray image output apparatus.

7. The X-ray image radiographing system of claim 1, wherein the plurality of X-ray image output apparatus are connected serially with a communication cable.

8. The X-ray image radiographing system of claim 1, wherein the plurality of X-ray image output apparatus are separately connected with the control apparatus by a separate communication cable.

9. The X-ray image radiographing system of claim 1, wherein the plurality of X-ray image output apparatus comprises plural different types of X-ray image output apparatus.

10. The X-ray image radiographing system of claim 9, wherein the plural different types of X-ray image output apparatus comprises a vertical type X-ray image output apparatus and a flat type X-ray image output apparatus.

11. The X-ray image radiographing system of claim 9, wherein the plural different types of X-ray image output apparatus comprises a fixed type X-ray image output apparatus in which a X-ray detector is fixed and a cassette type X-ray image output apparatus in which a cassette type X-ray detector is detachably mounted.

12. A X-ray image radiographing system for medical diagnosis, comprising:

a plurality of X-ray tubes each of which emits X-rays toward an object;

a plurality of X-ray image output apparatus each of which detects X-rays having passed through an object and outputs image data of a medical image of the object on a recording sheet on which the medical image of the object is reproduced for medical diagnosis;

a control device to correlate each of the plurality of X-ray image output apparatus with a respective one of the plurality of X-ray tubes; and a selecting device to select a specific X-ray tube among the plurality of X-ray tubes or to select a specific X-ray image output apparatus among the plurality of X-ray image output apparatus;

the control device controlling such that when the specific X-ray tube is selected, the selected X-ray tube emits X-rays toward an object and a X-ray image output apparatus correlated with the selected X-ray tube detects X-rays having passed through the object, or when the specific X-ray image output apparatus is selected, a X-ray tube correlated with the selected X-ray image output apparatus emits X-rays toward an object and the selected X-ray image output apparatus detects X-rays having passed through the object.

13. The X-ray image radiographing system of claim 12, wherein each of the plurality of X-ray image output apparatus has ID information.

14. The X-ray image radiographing system of claim 13, further comprising a storage device to correlate and store the ID information of a X-ray image output apparatus and image data outputted from the X-ray image output apparatus.

15. The X-ray image radiographing system of claim 12, wherein the control device comprises a first control device to selectively control the plurality of X-ray tubes and a second control device to selectively control the plurality of X-ray image output apparatus.

16. The X-ray image radiographing system of claim 15, wherein the first control device selects a X-ray tube corresponding to a X-ray image output apparatus selected by the second control device.

17. The X-ray image radiographing system of claim 15, wherein the second control device reads image data from a X-ray image output apparatus corresponding to a X-ray tube selected by the first control device.

18. The X-ray image radiographing system of claim 15, further comprising a radiographing condition inputting device, wherein the second control device reads image data from a X-ray image output apparatus selected by the radiographing condition inputting device.

19. The X-ray image radiographing system of claim 12, wherein a choice for a part to be radiographed is determined and indicted in accordance with a type of a X-ray image output apparatus.

20. The X-ray image radiographing system of claim 19, wherein the display device indicates a choice for a part to be radiographed.

21. The X-ray image radiographing system of claim 20, wherein the choice for a part to be radiographed is determined and indicted in accordance with a X-ray image output apparatus selected by the control device.

22. The X-ray image radiographing system of claim 19, wherein the display device indicates a choice for a radiographing direction.

23. The X-ray image radiographing system of claim 22, wherein the choice for a radiographing direction is determined and indicted in accordance with a type of a X-ray image output apparatus selected by the control device and a part to be radiographed.

24. The X-ray image radiographing system of claim 19, wherein a choice to select a plurality of radiographing directions at a time is included in the choice for a radiographing condition and is adapted to be registered.

25. The X-ray image radiographing system of claim 19, wherein when a part to be radiographed and a radiographing direction are selected as the radiographing condition, the display device indicates selection results sequentially.

26. The X-ray image radiographing system of claim 25, wherein the selecting device has a function to delete contents of the part and the radiographing direction.

27. The X-ray image radiographing system of claim 25, wherein the selecting device has a function to revise contents of the part and the radiographing direction.

28. The X-ray image radiographing system of claim 25, wherein the selecting device has a function to determines contents of the part and the radiographing direction.

29. The X-ray image radiographing system of claim 12, wherein the selecting device comprises a display device to indicate a choice for a plurality of radiographing conditions and selects one of the plurality of radiographing conditions.

30. The X-ray image radiographing system of claim 29, wherein the selecting device selects a specific X-ray image output apparatus in accordance with the selected radiographing condition.

31. The X-ray image radiographing system of claim 12, wherein the plurality of X-ray image output apparatus comprises plural different types of X-ray image output apparatus.

32. The X-ray image radiographing system of claim 31, wherein the plural different types of X-ray image output apparatus comprises a vertical type X-ray image output apparatus and a flat type X-ray image output apparatus.

33. The X-ray image radiographing system of claim 31, wherein the plural different types of X-ray image output apparatus comprises a fixed type X-ray image output apparatus in which a X-ray detector is fixed and a cassette type X-ray image output apparatus in which a cassette type X-ray detector is detachably mounted.

34. A X-ray image radiographing system, comprising:
- a X-ray image output apparatus to output image data based on a detection result of a X-ray image detector;
- a selecting device to select a radiographing condition including a part to be radiographed and a radiographing direction;
- an image processing device to process the image data; and
- a control device to change image data processing by the image processing device in accordance with a combination of a type of the X-ray image output apparatus, a type of the X-ray image detector, the selected part and the selected radiographing direction.

35. The X-ray image radiographing system of claim 34, wherein the control device discriminates whether the type of the X-ray image output apparatus is a X-ray image output apparatus employing a solid state flat plate detector or a X-ray image output apparatus employing a stimulable phosphor plate.

36. The X-ray image radiographing system of claim 34, wherein the control device discriminates whether the type of the X-ray image detector is a stimulable phosphor plate accommodated in a potable cassette or not.

37. The X-ray image radiographing system of claim 34, wherein the control device discriminates whether the type of the X-ray image output apparatus is a vertical type X-ray image output apparatus or a flat type X-ray image output apparatus.

38. A X-ray image radiographing system, comprising:
- a plurality of X-ray image output apparatus each of which outputs image data based on a detection result of a X-ray image detector;
- a control device to selectively control the plurality of X-ray image output apparatus; and
- an image processing device to process the image data;
- wherein the control device changes image data processing by the image processing device in accordance with a type of the selected X-ray image output apparatus, a type of the selected X-ray image detector.

39. The X-ray image radiographing system of claim 38, wherein when pixel values of the image data is almost linear to X-ray intensities, the image processing device conducts a predetermined image processing after conducting a logarithmic conversion for the image data, and when pixel values of the image data is almost linear to logarithmic values of X-ray intensities, the image processing device does not conduct a logarithmic conversion for the image data.

40. The X-ray image radiographing system of claim 38, wherein the image processing device conducts the image processing after conducting a correction process corresponding to a type of the X-ray image detector for the image data.

41. The X-ray image radiographing system of claim 38, wherein at least one of the image data processing conducted by the image processing device is a gradation converting process.

42. The X-ray image radiographing system of claim 38, wherein a content of a predetermined image processing conducted by the image processing device is a constant regardless of a type of the X-ray image detector.

43. The X-ray image radiographing system of claim 38, wherein a part of a content of a predetermined image processing conducted by the image processing device is changed in accordance with a type of the X-ray image detector.

44. The X-ray image radiographing system of claim 38, wherein the image data processing conducted by the image processing device is at least one of a gradation converting process, a frequency process and a dynamic range compressing process.

45. The X-ray image radiographing system of claim 38, wherein when the X-ray image detector is a solid state flat plate detector, a content of a correcting process conducted by the image processing device includes at least one of a gain correction and a offset correction, and when the X-ray image detector is a stimulable phosphor plate detector, the content of the correcting process includes at least one of a surface falling correction of a polygonal mirror used for a laser scanning device, a correction of an unevenness generated in a light collecting device for collecting stimulated light, a correction of an uneven sensitivity proper to a stimulable phosphor plate, and a correction of a sub-scanning unevenness generated in a conveying device.

46. The X-ray image radiographing system of claim 38, wherein a content of a correcting process conducted by the image processing device includes at least one of a correction for an image resolution of the image data, a correction for a density resolving power of the image data and a correction for a bit number per one pixel of the image data.

47. The X-ray image radiographing system of claim 38, wherein a content of a correcting process conducted by the image processing device is correlated with the image data and is stored in a memory.

48. The X-ray image radiographing system of claim 38, wherein the image processing device conducts the image data processing in accordance with a parameter representing a difference in a characteristic of image data caused by a difference in a characteristic of the X-ray image detector and a difference in an action of the X-ray image output apparatus.

49. The X-ray image radiographing system of claim 48, wherein the parameter is at least one of a parameter relating to an image resolution of the image data, a parameter relating to a density resolving power of the image data and a parameter relating to a bit number per one pixel of the image data.

50. The X-ray image radiographing system of claim 48, wherein the parameter is correlated with the image data and is stored in a memory.

51. The X-ray image radiographing system of claim 48, wherein the image data processing conducted by the image processing device is at least one of a gradation converting process, a frequency process and a dynamic range compressing process.

* * * * *